US008666482B2

(12) United States Patent
Wegerif

(10) Patent No.: US 8,666,482 B2
(45) Date of Patent: Mar. 4, 2014

(54) METHOD, SYSTEM AND SOFTWARE PRODUCT FOR THE MEASUREMENT OF HEART RATE VARIABILITY

(76) Inventor: Simon Christopher Wegerif, Southampton (GB)

(*) Notice: Subject to any disclaimer, the term of this patent is extended or adjusted under 35 U.S.C. 154(b) by 1077 days.

(21) Appl. No.: 12/565,717

(22) Filed: Sep. 23, 2009

(65) Prior Publication Data

US 2010/0174205 A1 Jul. 8, 2010

Related U.S. Application Data

(60) Provisional application No. 61/143,265, filed on Jan. 8, 2009.

(51) Int. Cl.
*A61B 5/04* (2006.01)

(52) U.S. Cl.
USPC .......................................................... 600/515

(58) Field of Classification Search
USPC .......................................................... 600/515
See application file for complete search history.

(56) References Cited

U.S. PATENT DOCUMENTS

| 2004/0015093 | A1  | 1/2004 | Knapp |
| 2004/0077934 | A1* | 4/2004 | Massad ........................ 600/300 |
| 2004/0117212 | A1* | 6/2004 | Kong et al. ........................ 705/2 |
| 2005/0177051 | A1  | 8/2005 | Almen |
| 2006/0063980 | A1  | 3/2006 | Hwang |
| 2006/0287605 | A1  | 12/2006 | Lin |
| 2007/0038135 | A1  | 2/2007 | Lin |
| 2007/0287928 | A1  | 12/2007 | Kiviniemi |

OTHER PUBLICATIONS

Great Britain Intellectual Property Office Search Report May 17, 2010.
Task Force of The European Society of Cardiology and The North American Society of Pacing and Electrophysiology (Membership of the Task Force listed in the Appendix), Guidelines, Heart rate variability, Standards of measurement, physiological interpretation, and clinical use, European Heart Journal (1996) 17, 354-381.
Carl Foster, A New Approach to Monitoring Exercise Training, Journal of Strength and Conditioning Research,2001,15(1),109-115.
Tran Thong, Kehai Li, James McNames, Mateo Aboy, Brahm Goldstein, Accuracy of Ultra-Short Heart Rate Variability Measures, EMBC 2003, 0-7803-7789-3/03/$17.00 ©2003 IEEE, 2424-2427.
Stephen W. Porges, The polyvagal perspective, Biological Psychology 74 (2007) 116-143, Available online Oct. 16, 2006.
Paul Montgomery and Ben Wisbey, Using Heart Rate Variability to Help Your Athletic Performance, FitSense Australia, http://www.transitionzone.com.au/content/physiology/Monitoring%20fatigue%20with%20HRV.pdf, Endurance Sports Training, 2009.

(Continued)

*Primary Examiner* — Christopher D Koharski
*Assistant Examiner* — Nadia Ahmad
(74) *Attorney, Agent, or Firm* — David Alan Bryan

(57) ABSTRACT

The invention relates to a method, system, and software product for measuring heart rate variability. The method comprises displaying an animation that indicates to the user when to breathe in and breathe out, receiving a signal from a sensor responsive to the heart beat of the user, processing the received signal to determine heart beat intervals of the user and calculating a measure of heart rate variability of the user from the processed heart beat intervals.

38 Claims, 13 Drawing Sheets

(56) References Cited

OTHER PUBLICATIONS

B. Wisbey, Using Heart Rate Variability to Help Your Athletic Performance, http://web.archive.org/web/20030430085442/www.endurancetraining.com.au/HRV.htm, Endurance Sports Training, Apr. 20, 2003.

Sweetwater Health, L.L.C., http://www.sweetwaterhrv.com/ ,Important Information for Users about Changes to the HRV Scale in SweetBeat™ v.1.2.2, http://www.sweetwaterhrv.com/documentation/ Explaining_New_HRV_Scale_Website.pdf ,Important Information for Sweetbeat™ Users, created Feb. 13, 2013, date of posting to website unknown, retrieved Mar. 11, 2013, pp. 1-3.

* cited by examiner

| DAY | S | M | T | W | TH | F | S |
|---|---|---|---|---|---|---|---|
| DATE | 7/1 | 7/2 | 7/3 | 7/4 | 7/5 | 7/6 | 7/7 |
| HRV | 50 | 54 | 60 | 64 | 70 | 60 | 50 |
| MOOD | 5 | 4 | 3 | 2 | 1 | 3 | 5 |
| MOOD | ☹ | ☹ | ☺ | ☺ | ☺ | ☺ | ☹ |

Fig. 9

METHOD, SYSTEM AND SOFTWARE PRODUCT FOR THE MEASUREMENT OF HEART RATE VARIABILITY

CROSS REFERENCE TO RELATED APPLICATION

This application claims the benefit of U.S. Provisional Patent Application No. 61/143,265, filed Jan. 8, 2009, and entitled Method for Convenient Daily Measurement of Heart Rate Variability, the entire disclosure of which is incorporated herein by reference.

COPYRIGHT NOTICE AND AUTHORIZATION

Portions of the documentation in this patent document contain material that is subject to copyright protection. The copyright owner has no objection to the facsimile reproduction by anyone of the patent document or the patent disclosure as it appears in the Patent and Trademark. Office file or records, but otherwise reserves all copyright rights whatsoever.

BACKGROUND OF THE INVENTION

1. Field of the Invention

The present invention is in the technical field of cardiac and autonomic nervous system function monitoring in human beings. More particularly, the present invention is in the technical field of Heart Rate Variability (HRV) measurements in human daily life.

2. Description of the Related Art

Heart Rate Variability (HRV) is based on the measurement of the time difference between each heartbeat, i.e., the beat-to-beat variability when processed using time domain, frequency domain or other measures, as described in "Heart rate variability: Standards of measurement, physiological interpretation, and clinical use", published 1996, Task Force of The European Society of Cardiology and The North American Society of Pacing and Electrophysiology, hereinafter referred to as "Task Force", and elsewhere. Each R-wave (of the P-Q-R-S-T sequence in ECG terminology) represents a forceful contraction of the heart and creates the pulse. The time difference between beats is known as the R-R interval. The beat-to-beat variability is affected by stimulation from the autonomic nervous system on the heart. The autonomic nervous system has two branches that usually work in an antagonistic manner: the sympathetic nervous system (SNS) that stimulates internal organs in preparation for "fight or flight" behavior, and the parasympathetic nervous system (PNS), that is associated with relaxation and allows humans to "rest and digest". The higher the level of PNS activity, the greater the freedom from physiological and psychological stress the person is experiencing. A good way to observe PNS activity non-invasively is to examine changes in heart rate in response to breathing. Heart rate increases during inhalation and decreases during expiration. This effect is known as respiratory sinus arrhythmia (RSA), and the changes in heart rate depend on breathing rate and depth (among other variables). High levels of PNS activity (as measured via RSA) indicate that the person is exhibiting a freedom from physiological and psychological stress. High parasympathetic HRV is known to be cardioprotective in the sense that persons with consistently high measurements of this parameter are less likely to suffer potentially fatal cardiac arrhythmia than persons with lower values. This principle may be used to measure relative changes in the effect of physical or mental stressors on an individual when their HRV is measured on a frequent (e.g., daily) basis, as described below in relation to one aspect of the invention.

The analysis and use of heart rate variability measurements has been established for more than 40 years, and has proven to have diagnostic and prognostic value in many clinical applications including, but not limited to: state of recovery following acute heart attack, work related stress level assessment, and fetal distress. Heart rate variability has also been used retrospectively to examine the impact of exercise and training that have already been performed by athletes, sedentary users and patients with existing cardiovascular disease.

At the current time, HRV is conventionally measured according to the Guidelines stated by the Task Force, by capturing ECG data gathered over periods ranging from 5 mins to 24 hrs using a clinical ECG apparatus or, for longer periods, a Holter recorder. The captured signals are first digitized and then processed using a frequency domain transformation in order to separate the markers of the two separate branches of the autonomic nervous system. In particular, the so called "High Frequency" band (defined as 0.15 Hz to 0.4 Hz) is associated with the parasympathetic (vagal) branch of the autonomic nervous system. The Task Force recommends short-term recordings of 5 min made under physiologically stable conditions processed by frequency-domain methods. A frequency domain transformation (e.g., Fast Fourier Transform) is recommended by the Task Force to have at least 512 data points in order to allow the accurate determination of power within the High Frequency band. This means in practice gathering approximately 6-9 mins of data for persons with resting pulse rates in the range 60-80 bpm. Interpolation of a lower number of data samples (e.g., 400) may also be used, but this still results in practical measurements of 5 minutes.

The present invention relies on the following principles:

1. Correlation between i) the current state of cardiovascular fitness and recovery in an individual, and ii) activity level of the parasympathetic (vagal) branch of the autonomic nervous system, observed conventionally via power level of HF modulation (HF power) in a frequency domain transformation of heart beat interval (R-R) data under consistent environmental and physiological conditions.

2. Mathematically proven, and empirically confirmed, relationship between time domain measured RMSSD and the more often used frequency domain measured HF power, recommended by the Task Force. RMSSD (ms), is the Root Mean Square Successive Difference, i.e., the square root of the mean of the sum of the squares of differences between adjacent normal RR intervals from short-term recordings or from an entire 24 hour electrocardiogram recording. This time-domain measure strongly reflects PNS modulation, and has also been shown to be mathematically equivalent to the Poincare SD1 measure times 1.414. The RMSSD measure has mainly been replaced in studies during the last 10 years by frequency domain analyses, since the latter give a more complete insight from the R-R interval data into the workings of multiple branches of the ANS. Nonetheless, the RMSSD time domain measure can give faster, accurate results when only the activity of the PNS is desired to be known.

3. High degree of correlation, and predictive accuracy, of ultra short term (e.g., 30 sec) versus more usual short term (5 min or greater) RMSSD measurements. Reference: "Accuracy of ultra short heart rate variability measurements", Engineering in Medicine and Biology Society, 2003, Proceedings of the 25th Annual International Conference of the IEEE. For example, the Task Force recommends short term RMSSD measurements.

4. Use of low frequency (typically <0.15 Hz), controlled deep breathing techniques during the measurement period in order to reduce the known impact of respiration rate and depth on HRV measurements, and also to help the user to relax, focusing the measurement result on physical (rather than mental) stress changes.

5. When possible, use of a static, standing position for measurement taking, avoiding supine saturation effects that can otherwise reduce the range of observed HRV measurements, especially in athletic individuals.

6. Recommendation to the user to take the daily measurement at about the same time each day, to further reduce variability, in this case caused by time of day induced (circadian) HRV variation.

SUMMARY OF THE INVENTION

The invention provides a method, system and computer software product for measuring heart rate variability of a user. As a first aspect of the invention, the invention provides a method of measuring heart rate variability of a user comprising displaying an animation that indicates to the user when to breathe in and breathe out, receiving a signal from a sensor responsive to the heart beat of the user, processing the received signal to determine heart beat intervals of the user and calculating a measure of heart rate variability of the user from the processed heart beat intervals.

As a second aspect of the invention, the invention provides a method of measuring heart rate variability of a user comprising instructing the user to breathe in and breathe out at predetermined times, receiving a signal from a sensor responsive to the heart beat of the user, processing the received signal to determine heart beat intervals and calculating a measure of heart rate variability from the processed heart beat intervals using a time domain processing method.

As a third aspect of the invention, the invention provides a method of awakening a sleeping user based on measuring heart rate variability, comprising receiving a signal from a sensor responsive to the heart beat of the user, processing the received signal to determine heart beat intervals, calculating a first measure of heart rate variability of the user from the processed heart beat intervals while the user is awake, calculating a second measure of heart rate variability of the user from the processed heart beat intervals while the user is asleep, computing the difference between the second measure and the first measure and generating an awakening stimulus to the user when the difference exceeds a predetermined threshold.

As a fourth aspect of the invention, the invention provides a system for measuring heart rate variability of a user, comprising means for displaying an animation that indicates to the user when to breathe in and breathe out, means for receiving a signal from a sensor responsive to the heart beat of the user, means for processing the received signal to determine heart beat intervals of the user and means for calculating a measure of heart rate variability of the user from the processed heart beat intervals.

As a fifth aspect of the invention, the invention provides a computer software product comprising coded instructions for executing a computer process in a digital processor, which computer process generates a measure of heart rate variability. The computer process comprises managing display of an animation that indicates to a user when to breathe in and breathe out, inputting processed heart beat intervals, wherein the processed heart beat intervals are output by a signal processing means and the input of the signal processing means comprises a signal received by a receiving means from a sensor responsive to the heart beat of the user, and calculating a measure of heart rate variability of the user from processed heart beat intervals.

As a sixth aspect of the invention, the invention provides a computer software product comprising coded instructions for executing a computer process in a digital processor, which computer process manages generating an awakening stimulus to a sleeping user by managing the measurement of heart rate variability. The computer process comprises inputting processed heart beat intervals, wherein the processed heart beat intervals are output by a signal processing means and the input of the signal processing means comprises a signal received by a receiving means from a sensor responsive to the heart beat of the user, calculating a first measure of heart rate variability of the user from the processed heart beat intervals while the user is awake, calculating a second measure of heart rate variability of the user from the processed heart beat intervals while the user is asleep, computing the difference between the second measure and the first measure and managing generating an awakening stimulus to the user when the difference exceeds a predetermined threshold.

The present invention comprises an improved method and system for taking, processing and presenting HRV measurements. The present invention captures signals generated by electrocardiographic (for example, chest strap ECG or other sensor of heart rate activity) or blood pressure (finger, earlobe, wrist or other) sensors in order to generate a heart rate variability index (for example, RMSSD or other time domain measure) more quickly, with higher repeatability and less need for training or expert instruction than previous methods.

The present invention collects, processes and displays HRV readings derived from electrocardiographic sensor data over a variable period while the user wears one of a plurality of sensors and breathes in a deep and controlled manner.

The present invention embodies the following aspects:

1. Use of very short term (1 min or less) versus more usual longer term (5 min or greater) HRV measurements 2. Use of low frequency (<0.15 Hz), controlled deep breathing techniques during the measurement period in order to reduce the impact of respiration rate and depth on HRV measurements. The combination of paced breathing and RMSSD can achieve reliable results in a short time.

3. Suggestion to the user via a number of possible methods including on screen display instructions or separate reference card, printed instructions or automated alarm clock function within the portable device itself to take the measurement at about the same time each day, to further reduce variability, in this case caused by time of day (circadian) induced HRV variation.

The above aspects provide an improved level of repeatability and convenience for periodic HRV measurements compared to current HRV measurement techniques, in particular the ability to use a mobile device to obtain an almost instant, reliable and repeatable reading (for example, 1 min is much shorter than conventional measurements taking at least 5 mins and possibly much longer), which can then be compared against measurements taken days, weeks, months or even years previously in order to gain insight on short, medium and long term HRV trends and fulfill a need for personal longitudinal data logging.

BRIEF DESCRIPTION OF THE DRAWINGS

The following detailed description will be better understood when read in conjunction with the appended drawings, in which there is shown one or more of the multiple embodiments of the present invention. It should be understood, however, that the various embodiments of the present invention are not limited to the precise arrangements and instrumentalities shown in the drawings.

In the Drawings:

FIG. 9 is an exemplary pictorial representation of a portion of the user interface for displaying HRV and mood information.

DETAILED DESCRIPTION

Figure 1:
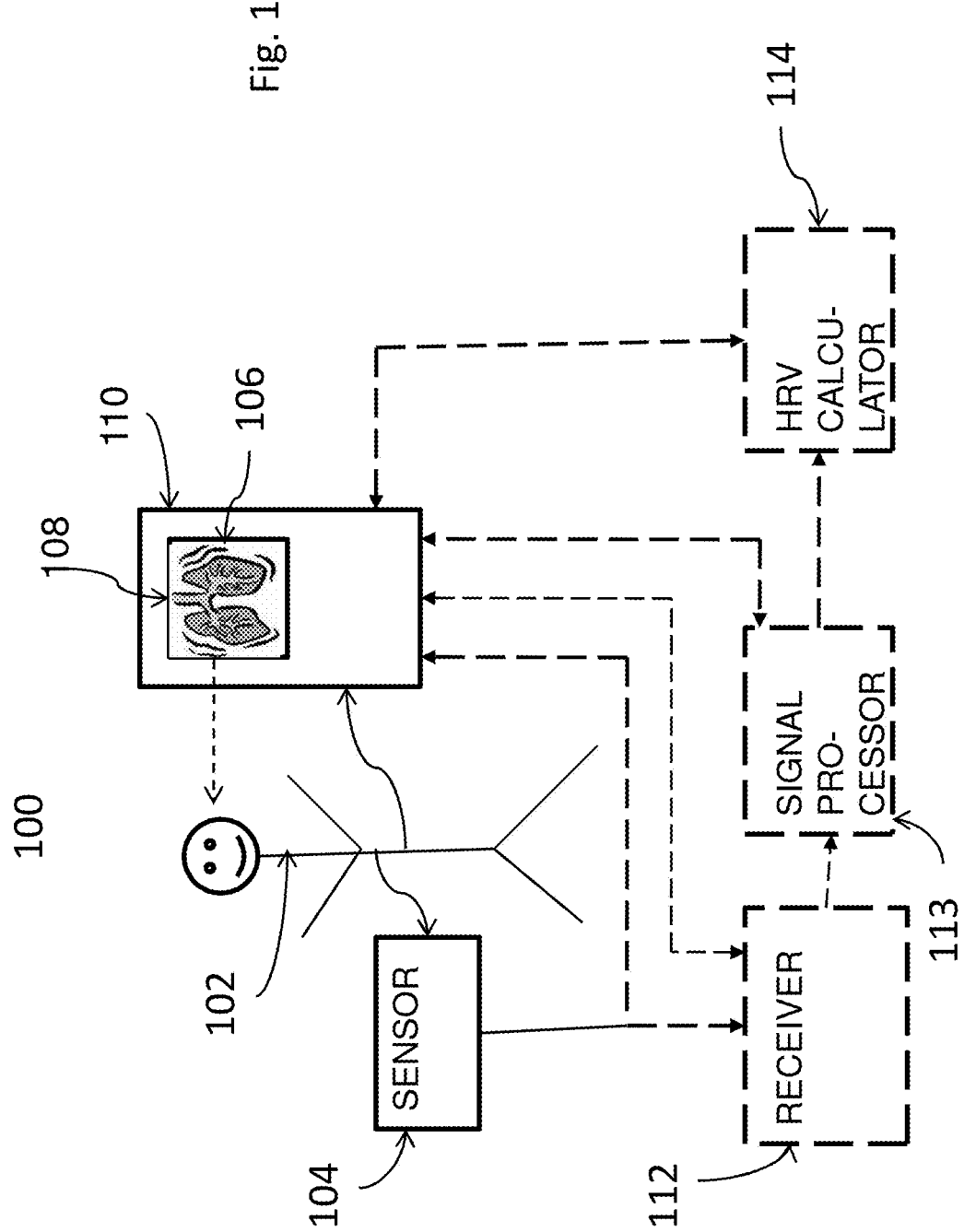
FIG. 1 is an exemplary overview of the method and system for HRV measurement.

Referring now to FIG. 1, there is shown one general exemplary functional embodiment of a system 100 for measuring heart rate variability of a user 102. The user 102 may put on a sensor 104, for example, a commercial chest ECG sensor strap. An animation 106 that indicates to the user 102 when to breathe in and breathe out may be shown on display function 108, for example, an LCD display forming part of, for example, a handheld portable device 110. Animation 106 may be displayed by hardware and/or software known in the art, for example display generation software and hardware within device 110. Alternatively, display function 108 may be realized by any suitable type of display that comprises part of a portable or non-portable device, or it may be a self-contained display device connected by wire or wirelessly to device 110 (not shown in FIG. 1). The signal from sensor 104 may be processed by receiver function 112, for example, to demodulate the sensor signal and convert it to a digital format. Receiver function 112 may be realized in hardware and/or software known in the art, for example, a receiving antenna in hardware followed by A/D conversion, filtering and demodulation in software and/or hardware. The output of receiver function 112 may be processed by signal processor function 113, for example to reliably generate heart beat intervals for HRV calculation by HRV calculator 114. Signal processor function 113 may be realized in hardware and/or software, for example, by a counter/timer function in software and/or hardware. HRV calculator 114 may be realized in hardware and/or software, for example, by software running on a digital CPU, special purpose digital hardware, or a combination of software and hardware.

In one embodiment of the present invention, animation 106 may indicate to the user to breathe in for a count of S1 (for example, S1=3) seconds and out for a count of S2 (for example, S2=5) seconds, with this sequence to be repeated 4 or more times within a measurement time window.

In some embodiments, a first sound, for example, the sound of advancing ocean waves, may be generated, for example by device 110 to indicate to the user 102 when to breathe in, and a second sound, for example the sound of retreating ocean waves, may be generated by hardware and/or software known in the art, for example, by software running on a digital CPU, special purpose hardware, or a combination of software and hardware, within device 110 to indicate to the user 102 when to breathe out. Alternatively, these sounds may be generated by external functions connected to device 110 (not shown in FIG. 1).

In some embodiments, sensor 104 may be closely attached to or within device 110. In these embodiments, device 110 may, for example, be placed on the skin or clothing of the user 102 by the user or another individual, for example, a medical technician.

In some embodiments, the signal from sensor 104 may be connected by wire to device 110. Alternatively, the signal from sensor 104 may be connected wirelessly to device 110; in these embodiments, receiver function 112, signal processor function 113 and HRV calculator function 114 may comprise part of device 110. Alternatively, receiver function 112 and/or signal processor function 113 and/or HRV calculator function 114 may be external to device 110. Receiver function 112 and/or signal processor function 113 and/or HRV calculator function 114 may, for example, be realized by one or more physical modules that plug in to device 110, using connectors and signaling protocols known in the art. Functions 112-114 may all be realized in one physical module or in many modules, e.g., FIG. 1 should not be understood to imply a one-to-one mapping between functions and physical modules.

In some embodiments, for example in embodiments where one or more of functions 112-114 are external to device 110, analog and/or digital connections, of types known in the art, shown by dashed lines in FIG. 1, may convey signals back and forth among the subset of functions 112-114 that are external to device 110 and among each other, as appropriate to exchange the information necessary to carry out the functions of processing stages 112-114. The connections represented by dashed lines in FIG. 1 may be realized using any number of wired conductors or wireless links, and may employ multiplexing techniques to minimize the number of such conductors and/or links, as known in the art. Dashed lines are shown as bidirectional in FIG. 1 to include the exchange of control and/or intermediate results of processing calculations, as appropriate, between processing stages 112-114 and device 110, however, the basic heart rate information processing sequence is from sensor 104 to receiver function 112 to signal processor function 113 to HRV calculator function 114. In some embodiments where both the signal processor function 113 and the HRV calculator function 114 are external to device 110, the output of signal processor function 113 may be connected to both the HRV calculator function 114 and directly to device 110, for example, so that processed heart beat intervals may be conveyed to device 110 as well as to HRV calculator function 114.

In some embodiments, synthesized audio may instruct the user 102, for example, on how to place the sensor 104, and/or when to breathe in and breathe out, and/or when the measurement is complete. In some embodiments, the synthesized audio may also deliver the results of measurements and/or computations to the user 102. Synthesized audio may be generated by hardware and/or software known in the art, for example, by a combination of software running on a digital CPU and D/A conversion hardware within device 110. Alternatively, these sounds may be generated by external functions connected to device 110 (not shown in FIG. 1).

In some embodiments, audible commands and/or responses may be received from the user 102. For example, the user 102 may say "start" to cause the system to begin a HRV measurement. Audible input may be recognized by hardware and/or software known in the art, for example, by a combination of A/D conversion hardware and software running on a digital CPU and within device 110. Alternatively, these sounds may be received and/or recognized by external functions connected to device 110 (not shown in FIG. 1).

Figure 2:
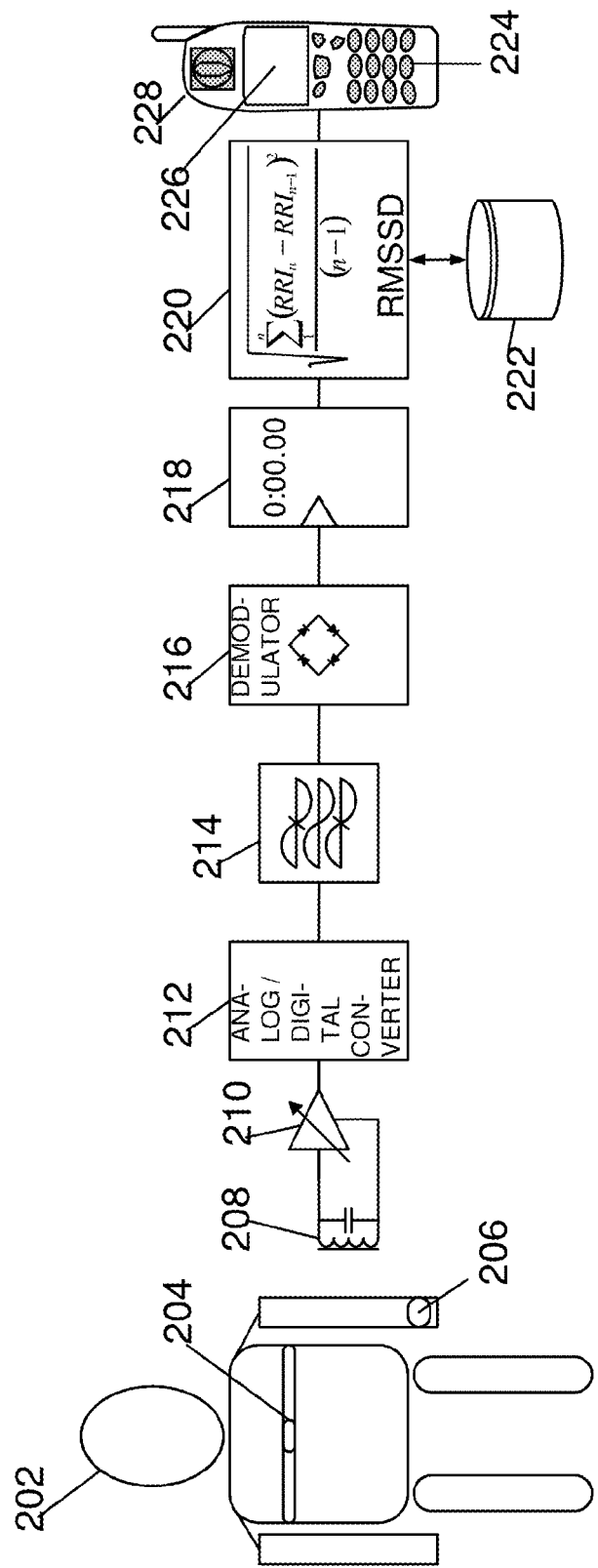
FIG. 2 is an exemplary diagrammatic view of the series of signal processing steps of one embodiment.

Referring now to FIG. 2, in one exemplary embodiment, there is shown the frontal view of a user 202, who is in a static, standing up (orthostatic) position preferred for taking a heart rate variability measurement. The user 202 may first put on either a commercial chest ECG sensor strap 204 (not part of the present invention) which may use, for example, 5.3 kHz amplitude modulated inductive transmission techniques to send ECG signals to the resonant antenna 208. Due to the use of inductive transmission, the resonant antenna 208 has to be in close proximity (<1 m) to the chest strap sensor 204. Alternatively a commercial ECG, wrist, ear or finger cuff blood pressure sensor 206 may be connected, for example via a cable (not shown in FIG. 2), to the amplifier 210.

The received signal in antenna 208 may consist of bursts of 5.3 kHz amplitude modulation at a level of a few millivolts (mV), so the inductor and capacitor values should be appropriately chosen to be resonant at this frequency. Alternatively, just an inductor, instead of the resonant circuit 208, may be used, but the antenna efficiency and therefore useful working range of the transmission will be reduced. The received signal may be amplified by high gain amplifier 210, before being converted to the digital domain by analog to digital converter 212. The latter should have dynamic range of at least 8 bits, and sample rate at least twice the received signal bandwidth to avoid aliasing (Nyquist criterion). In one embodiment, processing stages 210 and 212 are provided by the microphone input of, for example, the mobile device 228.

Once digitized, the signal, for example in case of origination from a commercial ECG chest strap, may be bandpass filtered with center frequency of 5.3 kHz in filter 214. Since the received signal is amplitude modulated, the envelope of the signal may be recovered by demodulator 216. This may be achieved, for example, by conventional full wave rectification and low pass filtering. The successive rising edges of the resulting demodulated signal may then be used to start and stop a counter-timer 218, which according to Task Force guidelines should have measurement precision better than 2 ms. In order to prevent false triggering from noise signals, ectopic beats, or non-ECG coding signals in the chest strap transmission, the counter-timer 218 may run for a minimum of 500 ms before it is allowed to be reset. This exemplary value is chosen under the expectation that a user 202 taking readings in the preferred stationary standing position would have a heart rate lower than 120 beats per minute. In one embodiment, processing stages 214-218 are performed by hardware and/or software modules within mobile device 228.

The output from counter-timer 218 is a series of consecutive R-R Interval (RRI) values, measured in milliseconds (ms), with a new value being sent to statistical processor 220 about once per second, equivalent to the heart rate of the user 202, normally around 60 beats per minute. In statistical processor 220, in one exemplary embodiment, the Root Mean Squared Successive Difference (RMSSD) may be calculated according to a conventional formula:

$$RMSSD = \sqrt{\frac{\Sigma_1^n (RRI_n - RRI_{n-1})^2}{(n-1)}}$$

as shown in block 220 of FIG. 2. This process involves first squaring the adjacent R-R Interval (RRI) differences, and incrementing the value of n each time a new sample is received from counter-timer 218. Elimination of irregular beat data may be achieved, for example, by looking for any RRI squared values greater than 40000, which would indicate a RRI to RRI difference of more than 200 ms, which is very unlikely to occur in normal sinus heart rhythm. Any value greater than 40000 is therefore not added to the running total sum; neither is the n value of the divisor in statistical processor 220 incremented in that case. Subject to this exception, the resulting RMSSD value may be updated every time a new RRI value is received from counter-timer 218, and displayed in both textual and graphic form on the display 226 of the portable device 228. Values of RRI and RMSSD may be stored in database 222. In one embodiment, processing stages 218-222 are performed by hardware and/or software modules within mobile device 228.

Alternatives to RMSSD are pNN50, the probability of any NN (normal-to-normal RR after exclusion of irregular beats) interval difference exceeding 50 ms, and the SD1 parameter of the cluster Poincare plot (2D plot of adjacent R-R intervals), as described in the Task Force paper references for time domain heart rate variability measures.

In the embodiment of FIG. 2, processing stages 208-216 may represent an example of a more detailed functional representation of the receiver function 112, processing stage 218 may represent an example of a more detailed functional representation of the signal processor function 113, and processing stages 220-222 may represent an example of a more detailed functional representation of the HRV calculator 114. Any subset of functions 208-222 may be implemented internally to device 228. Alternatively, any subset of functions 208-222 may be implemented externally to device 228. In one embodiment, antenna 208 may be external to device 228 while functions 210-222 may be internal to device 228.

Figure 3:
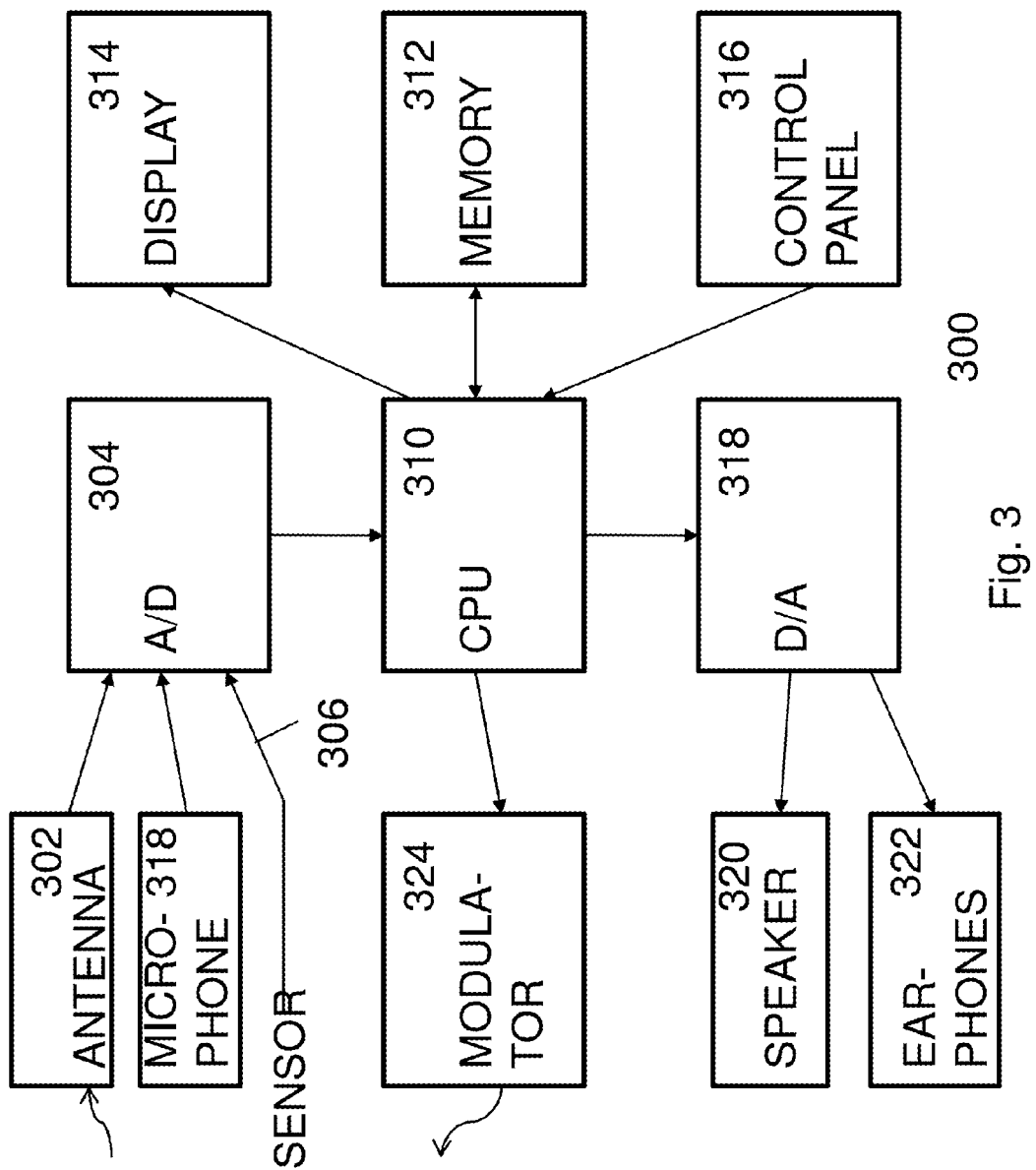
FIG. 3 shows an exemplary decomposition of the system into functional units.

Referring now to FIG. 3, there is shown one exemplary functional embodiment of the system for measuring heart rate variability. Heart rate related signals may be received from a sensor, for example, sensor 204, via an antenna 302. These signals may be amplified by an amplifier (not shown in FIG. 3), for example, amplifier 210, before being converted to digital form by an analog-to-digital converter (A/D) 304, which may comprise the A/D converter 212 in some embodiments. Alternatively, A/D converter 304 may receive heart rate related signals from a sensor, for example sensor 206, via connection 306, which may comprise, for example a cable. In some embodiments, connection 306 may be bisected by amplification and/or filtering (not shown in FIG. 3) between the sensor end of connection 306 and the A/D converter 304 end of connection 306. A/D converter 304 may also convert analog audio signals from an audio transducer, for example, microphone 308, for example in embodiments where the user interface includes speech recognition capability. The digitized sensor signals may be received by central processor (CPU) 310. CPU 310 may be controlled by instructions stored in a portion of the address space of memory 312. In some embodiments, CPU 310 may further process the digitized sensor signals, for example, by filtering as described previously with reference to block 214, and by demodulating as described previously with reference to block 216. In some embodiments, CPU 310 may detect heart rate intervals by implementing a counter/timer-type function, for example, as described previously with reference to block 218. CPU 310 may perform heart rate variability calculations, for example the RMSSD calculations as described previously with reference to block 220. CPU 310 may store and/or recall intermediate and/or final results of the heart rate variability processing using memory 312. CPU 310 may, for example, prompt for user input and/or generate instructions to the user and/or display results to the user using display 314, which may comprise display 226 or 108 in some embodiments. CPU 310 may receive user input via control panel 316, which may comprise control panel 224 in some embodiments. In some embodiments, CPU 310 may generate sounds, for example to indicate to the user when to breathe in and breathe out, as previously described, using digital-to-analog (D/A) converter 318 and speaker 320. Alternatively, sounds may be provided to earphones 322. Instructions to the user may also be given, for example by software running on CPU 310 by retrieving digitized speech from memory 312 and generating analog speech sounds using D/A 322 and speaker 320.

It is important when processing heart rate variability signal measurements to be able to detect irregular R-R intervals caused by multiple sources, including ectopic beats, missing beats originating from the heart, and transmission errors between, for example, the chest strap 204 and the wireless receiver 208. Such irregular R-R intervals can cause significant errors and distortion in the final calculation result, leading to incorrect decisions. A series of R-R intervals processed to remove irregularities is known as an N-N interval series. The gold standard for such processing includes a review of the data by an experienced electrocardiographic (ECG) technician.

In some embodiments, the present invention includes a method for automating the periodic measurement of HRV, and thus in these embodiments there is no opportunity for manual review of the measured R-R intervals. This necessitates the inclusion of more sophisticated means of detection of R-R intervals that are likely to be invalid. This process is assisted by the fact that the current movement status (standing still) and breath state (i.e., exhaling or inhaling following, for example, a lungs animation 106) of the user is known.

Figure 4:
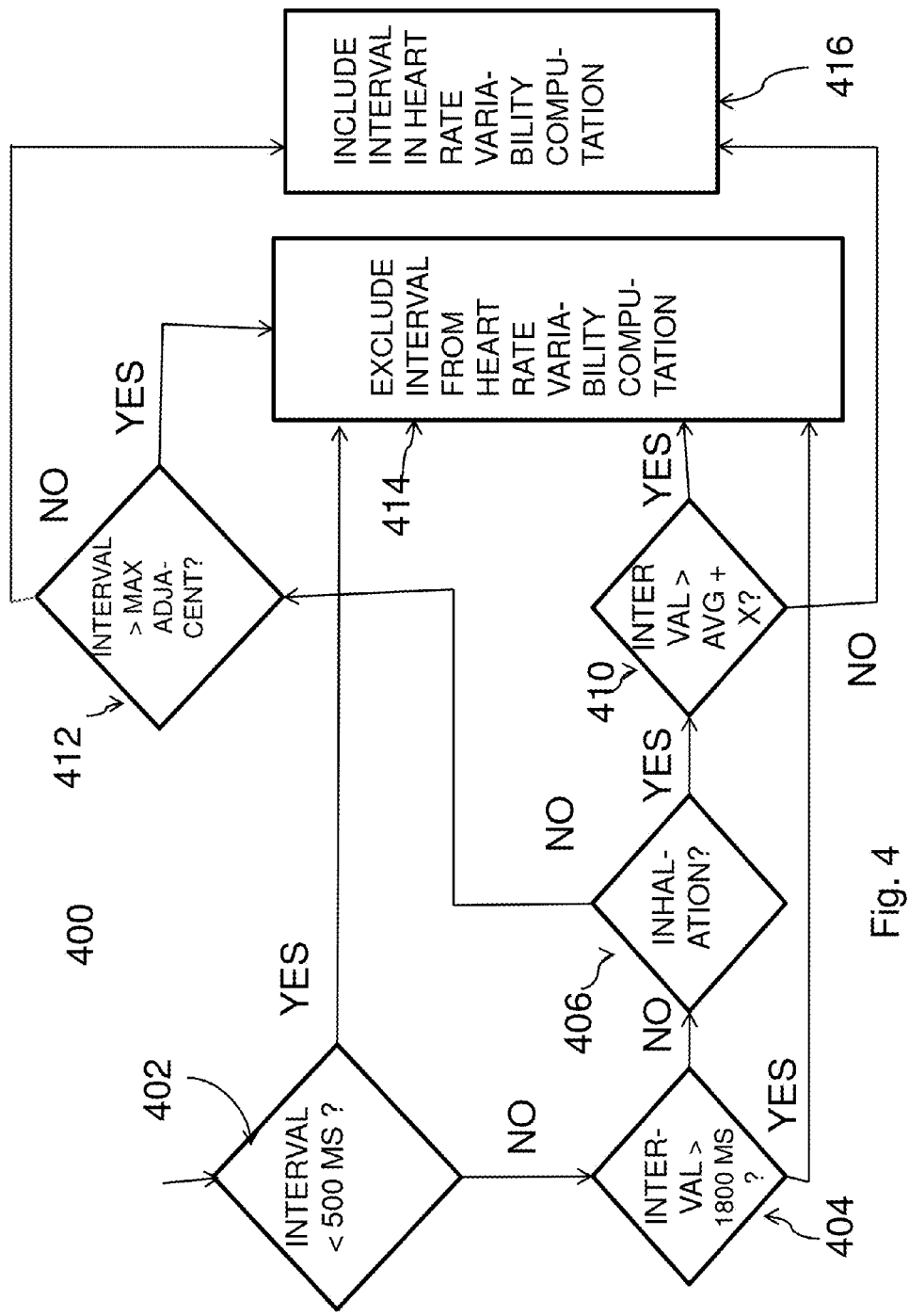
FIG. 4 is an exemplary flow chart of one aspect of the heart rate processing.

In some embodiments, irregular R-R intervals may be excluded from the HRV calculations, e.g., the RMSSD calculations of processor 220, according to the method illustrated in FIG. 4. In FIG. 4, at steps 402 and 404 if at any time the measured R-R interval is either shorter than 500 ms, or longer than 1800 ms that R-R interval may be excluded at step 414 on the basis that it is not a reasonable value for a human being in the standing position. Irregular intervals may be excluded by hardware and/or software, for example, by software running on digital CPU 310 and/or special purpose counter/timer hardware, for example a hardware realization of function 218.

During inhalation, as identified at step 406, the autonomic nervous system (parasympathetic branch) of the user withdraws stimulation, with the consequence that the R-R interval is shortened. Since the method, for example as previously described with reference to FIGS. 1 and 2, includes a controlled breathing pattern, beats that are longer than the average R-R interval taken (which may be calculated over one or more complete breath cycles) during inhalation may be identified at step 410 and excluded at step 414. In practice an additional margin, shown as x in step 410, may be included to allow for the fact that the user's breathing may not be perfectly synchronized with, e.g., the lung animation 106 of FIG. 1.

During exhalation, as identified as not-inhalation at step 406, a maximum allowed difference between adjacent R-R intervals can also be predicted by knowing the average R-R interval taken over one or more complete breath cycles during the measurement. This is possible because the parasympathetic-sympathetic balance also controls the standing pulse rate. A formula has been determined empirically from observations on multiple users, whereby the maximum permitted R-R interval difference may be related to the square of the mean R-R interval (measured in milliseconds) divided by a constant, for example 12000. Therefore, R-R intervals not conforming to:

Max allowed adjacent R-R interval difference=(mean R-R interval)$^2$/12000 may be identified at step 412 and excluded at step 414. In some embodiments, the measurement sequence may include preliminary breathing cycles, during which the mean R-R interval is calculated, before the HRV calculation begins, so that non-valid R-R intervals may be excluded right from the start. Intervals not identified for exclusion according to the preceding criteria are included in the HRV calculations, e.g., the RMSSD calculations of processor 220, at step 416.

In the case that a user has a temporarily irregular heart rhythm, such as palpitations, Atrial Fibrillation, or SupraVentricular Tachycardia, this may lead to a number of excluded intervals according to the set of rules outlined in the previous paragraphs. In case the number of such excluded beats exceeds a predefined threshold, e.g., 5, during the measurement sequence, then the measurement will be terminated and the user informed of the reason, and instructed to retake the measurement after some period of time. This is in order to prevent incorrect readings from contaminating the calculation of longitudinal averages and other statistical measures upon which recommendations may be based.

Figure 5:
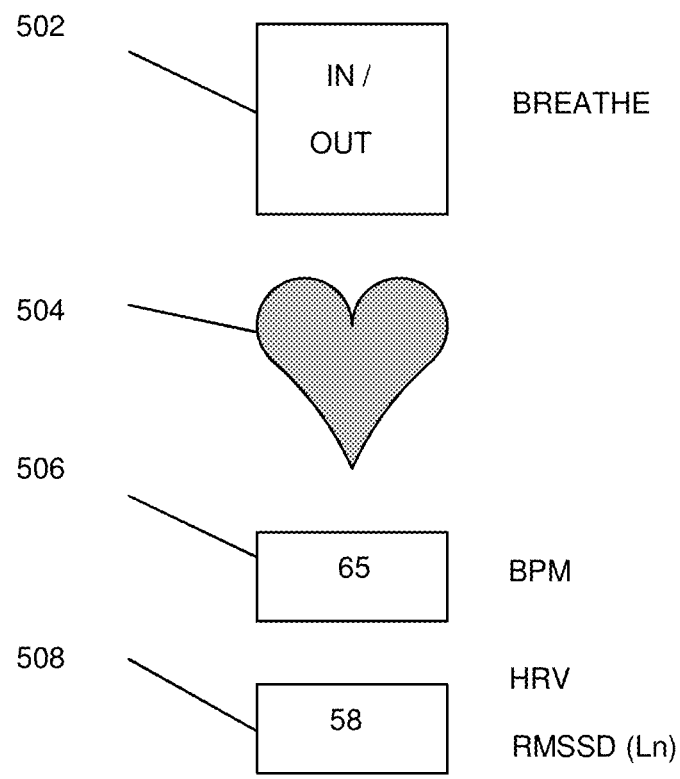
FIG. 5 is an exemplary pictorial representation of the user interface while the HRV measurement is taking place and at its completion.

Referring again to FIG. 2 and now to the interaction between the invention and the user 202, the measurement may first be initiated using the controls 224, which may be buttons, touch screen or other suitable method provided, for example, on portable device 228 in FIG. 2. FIG. 5 shows the user interface displayed on a mobile phone, or other personal device with similar processing and display capabilities, during and at the conclusion of the measurement. During an HRV measurement, indicator 502 may prompt the user to breathe in and then out in a controlled manner and for predefined time periods in each breathing phase using a graphical animation (e.g., a pair of expanding lungs 106 as shown in FIG. 1), or using sounds or other stimuli as described in earlier paragraphs. The overall breathing frequency should be low enough not to significantly alter the amplitude of the HRV measurements.

Heart shaped indicator 504 may be displayed on display 226 and pulse according to the output of demodulator 216 in FIG. 2, to show the user 202 that a valid heart rate signal is being received from sensor 204 or 206. Potential problems include a weak signal caused by excessive distance between sensor 204 or 206 and receiver coil 208, or poor placement or contact of the sensor 204 or 206. In this case, the user 202 may be informed by on-screen (for example, 226) instructions to make the necessary adjustments.

At the conclusion of an HRV measurement, numeric indicator 506 may show the average heart rate in beats per minute, a measurement also derived from demodulator 216 in FIG. 2, and a reading with which most users will be familiar. This provides further confirmation of a good received signal, and provides additional basic heart rate monitor functionality. Indicator 508 may show the calculated RMSSD value output from block 220, which is updated on display 226 every time a new valid RR Interval is processed. The raw RMSSD value may be further processed in order to derive a scale with benefits for end users and medical personnel. For instance, a logarithm, e.g., the natural logarithm, of the RMSSD value may be taken and multiplied by a scale factor, e.g., 20, to generate a HRV index; these operations may be realized in hardware and/or software, for example, by software running on CPU 310, special purpose digital hardware, or a combination of software and hardware, using techniques known in the art. This results in a scale with approximate maximum 100 for humans with very high heart rate variability, such as elite athletes, and close to 0 for a heart rhythm with no short term variability, such as may be found in a denervated or paced heart, or a subject in a mental state of coma. It also means that changes over a period of time result in constant numeric additive or subtractive offset values independent of starting number. This can be very useful for comparing the impact of stressful events such as athletic training & competition between users, and can also allow these changes to remain of similar value as the user's steady state HRV levels change, e.g., due to increase/decrease in fitness, or due to aging. The measurement is completed after a predefined number of breathing cycles, in one embodiment 7 cycles of 8 seconds giving a measurement time of 56 seconds.

Figure 6:
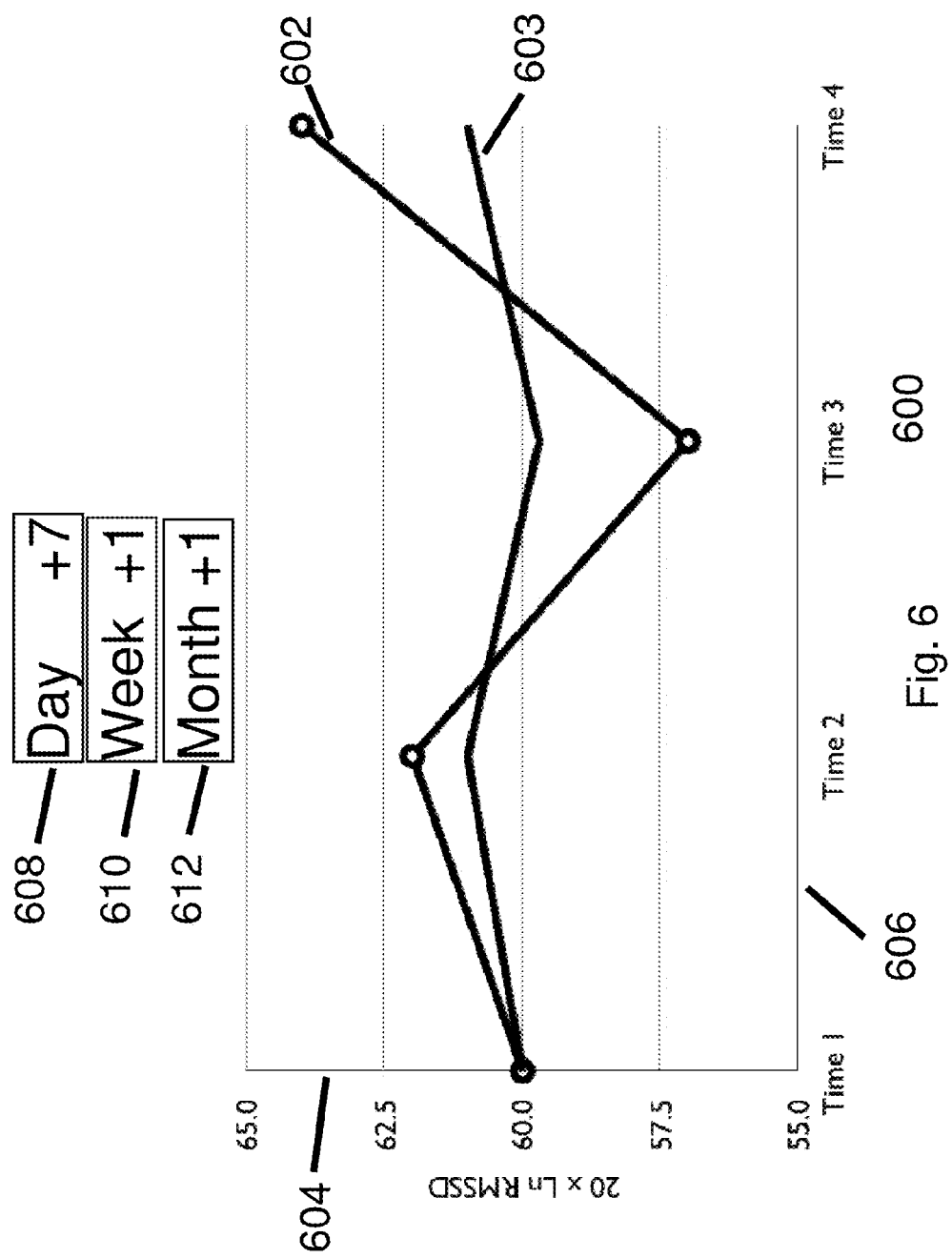
FIG. 6 is an exemplary pictorial representation of the user interface for presenting results of the HRV measurements.

Referring now to FIG. 6, the most recent HRV index measurement is displayed in the context of previous measurements by means of graphic line 602, in order that the user may easily visualize significant day to day changes, as well as long term trends. The time axis 606 may be linear, with 4 different timescales, for example, 1 week, 1 month, 3 months, all data. For example, two lines may be shown: daily points joined by straight segments (line 602) and rolling 7 day average line 603. Example thresholds may be based on absolute unit changes or may be statistically derived from current and previous HRV index measurements. An initial 1 day significant decrease may be shown in amber, a further significant decrease on subsequent days may be shown red. Alternatively, the time axis 606, may be displayed in logarithmic form in order to show discrete data points and emphasize changes over most recent days while still being able to visualize long term trends over months or even years. Numeric indicators 608, 610 and 612 may show differences between the most recent reading and that of the previous day, week and month respectively. These indicators may optionally be colored to show trends with example thresholds of 4 HRV index units in either direction. For example, in particular, an increase of 4 could be considered beneficial and be colored green, whereas a decrease of 4 could be considered harmful, and shown in red. Changes within these limits might remain with a neutral color, or alternatively, may progressively shade green or red. The entire chart area between axes 604 and 606 may optionally also be shaded from red at HRV index 20 to green at HRV index 100, with the region around HRV index 50-60 being neutral yellow.

Since exercise is an important part of maintaining cardiovascular health, it may be useful to track a training load quantity which is independent of the type of sport performed, as a method of capturing the duration and perceived effort level of the user. In some embodiments, such a metric, for example, session RPE (Rating of Perceived Exertion) as proposed by Foster et. al. in Sports & Conditioning Research Journal 2001; 15(1), 109-115 is tracked. For example, the RPE value may be captured on a 1-10 scale and multiplied by the exercise duration in hours in order to obtain a Training Impulse (TRIMP) score. It is proposed to take this method of capturing the duration and perceived effort level of the user. For example, the user 202 may be instructed to choose an exercise duration that best fits their session from a drop down list displayed on the user interface 226, or they may enter a value using input device 224. This recording of periodic training load values by the user may be realized by hardware and/or software, for example, by display device 226, input device 224 and software running on a CPU, such as CPU 310, within device 228. The Perceived Exertion rating may be derived as per the reference using, e.g., a 10 point scale, again entered using microphone 318 or data entry mechanism 224. Alternatively, the TRIMP score may be entered directly from, or based on calculations from a heart rate monitor device worn by the user during exercise. The measure of training load, for example, the Training Impulse score, may be stored in, and subsequently retrieved from a database, for example, the same database 222 containing the periodic HRV readings, or alternatively, a second database, by hardware and/or software, for example, memory control hardware and software known in the art. Subsequently, the periodic training loads may be displayed on, for example, display 226, e.g., as a histogram as part of a chart displaying HRV readings, to allow an easy visual correlation between exercise level and changes in HRV. An illustrative example could be a recreational athlete who is training for an event, but who does a number of hard training sessions on consecutive days. It is likely that their HRV daily readings would decline, and they would be able to associate this with the training load columns of the chart, make adjustments to their training schedule, for instance to increase the amount of rest and recovery, thereby leading to an optimization in daily HRV readings. The histogram may be computed in hardware and/or software, for example, by software running on a digital CPU such as CPU 310, special purpose digital hardware, or a combination of software and hardware.

Figure 7:
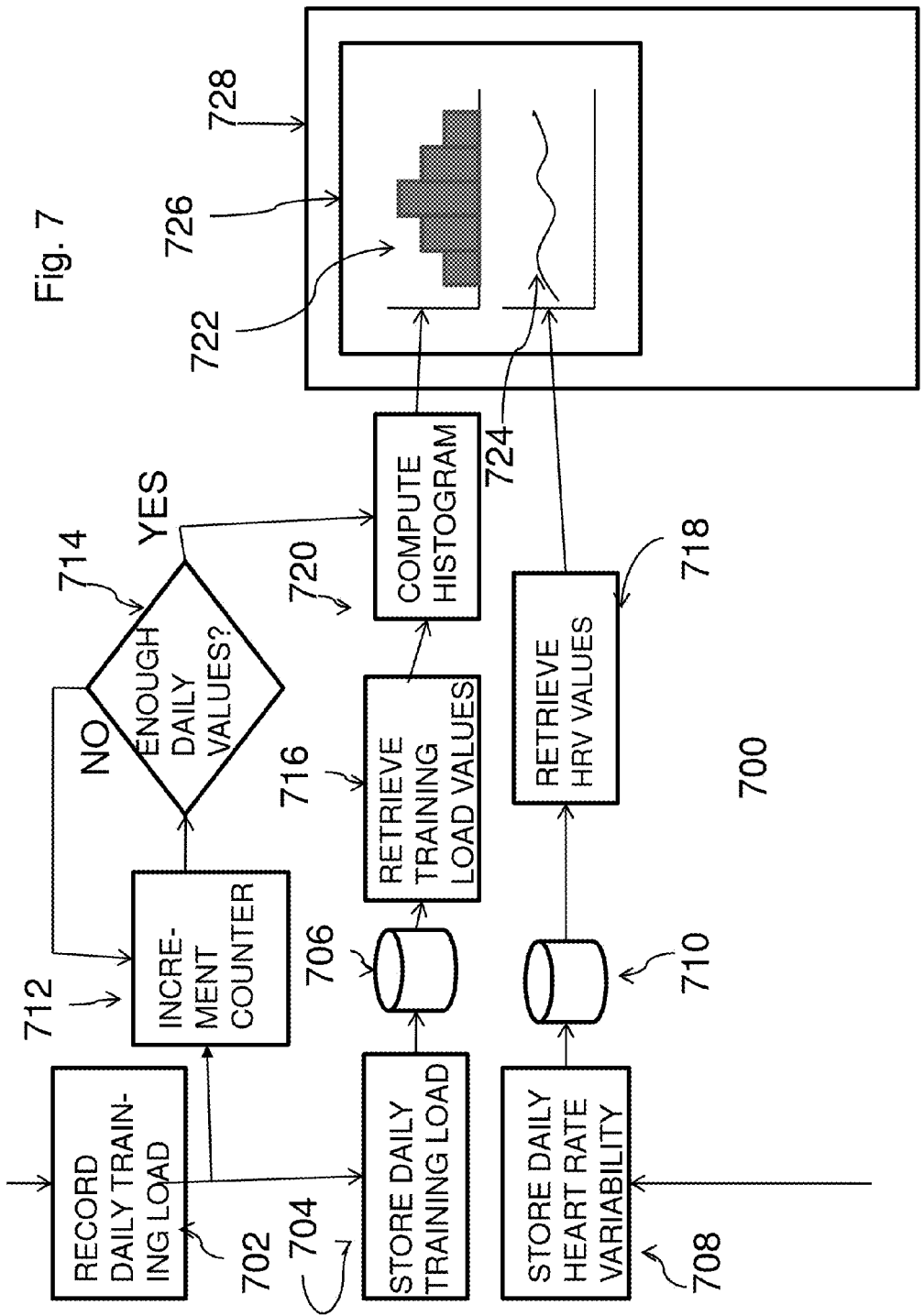
FIG. 7 shows an example of the steps of the computation and display of training load and HRV results.

Referring now to FIG. 7, daily training load is recorded by the user at step 702. This may, for example take the form of user 202 keying in a value, for example, the RPE value, using control panel 224 of portable device 228. Alternatively, user 202 may enter the value into device 228 verbally, in embodiments wherein device 228 supports speech recognition. Daily training load and HRV are stored in databases 706 and 710 (which may comprise portions of the same database, e.g., database 222 in some embodiments), at steps 704 and 708, respectively. Using counter 712, at step 714 it is determined, for example by software running on CPU 310, whether enough daily values of training load have been stored in database 706 to be able to compute a valid histogram of training load, at the first instance of accumulating training load and HRV values, and/or subsequently, after a reset of counter 712 initiated by the user using, for example, a user interface (for example control panel 224 of FIG. 2 in some embodiments) of device 728 (for example, device 228 of FIG. 2 in some embodiments). The value of counter 712 may for example be stored in a memory 312 by CPU 310. At steps 716 and 718, values of training load and HRV may be retrieved from databases 706 and 710, respectively, for example after a command to display a comparison chart of training load and HRV is entered by user 202 using control panel 224, in some embodiments. At step 720, a histogram of training load may be computed, for example, by CPU 310 over a user-selected time period and presented to the user 202 visually, for example as bar-type chart 722, on display 726 of device 728. A line-type chart 724 comprising HRV values for substantially the same time period as that for which the histogram 722 is computed may also be presented at substantially the same time on display 726 of device 728.

In some embodiments, recommendations to end users may be presented, based on the sequence of daily readings, and in particular their relative values over time. In general, recommendations presented by the invention may, unless otherwise described herein, be presented using any combination of hardware and software. In particular these recommendations may be presented using, for example a display such as display 226, and/or by audible output using, for example, a combination of software running on CPU 310, D/A converter 318 implemented in hardware, and speaker 320 or earphones 322 connected to, for example device 228. Although these recommendations for athletes may be presented in numerous ways, they may be especially helpful when they are under 3 simple headings.

1. REST—avoidance of training for a period of time
2. TRAIN—undertake structured training at different intensity and volume levels
3. COMPETE—indicate that based on HRV readings, the user is currently likely to be capable of good performance levels in a forthcoming event The theory relating to parasympathetic HRV that underpins these directions is as follows:

1. REST. A significant (as assessed by statistical tests, known in the art, on previous daily values) decline in daily reading from one day to the next independent of all other indications indicates that the user's body is experiencing a significant physiological or psychological stress from which they need some period of time to recover.

2. TRAIN. A reading which is in line with, or above the recent trend (assessed by geometric mean or other averaging technique) of readings, and assuming that there are no contraindications from HRV or other symptoms in the user.

3. COMPETE. The theory of periodization indicates that in order to maximize performance in competition, a period of strenuous training (also known as functional overreaching) should be followed by a period of lighter training or rest in order for super-compensation (when the body becomes stronger) to occur. Sports coaches have discovered that the period of rest should be followed by some intense sessions to prepare the body for the rigors of competition.

In HRV sequence terms, this means that a depressed mean value during training may be followed by a significant rise in the mean value (likely to a level higher than seen in previous months) during recovery, followed by a dip before competition.

For example, the present invention, may have indicators for 3 time periods, respectively: a) Daily Change, b) Weekly Change, c) Monthly Change All 3 indicators may assume any of the following color values with associated significance:

1. Blue (B)—no significant change
2. Amber (A)—significant negative change
3. Red (R)—highly significant negative change
4. Green (G)—significant positive change Putting together the above desired recommendations and indicators, may give the following table of interpretations:

|  |  | Daily Change | Weekly Change | Monthly Change |
|---|---|---|---|---|
| Rest | Rest for one day | R | G/B/A | G/B/A |
|  | Rest for 2-3 days | A | A/R | B/A |
|  | Rest several days | R | A | A |
|  | Extended rest | R | R | R |
| Train | Light training | A | G/B | G/B |
|  | Normal training | B | G/B | G/B |
|  | Intense training | G | G/B | G/B |
| Compete | Ready to compete | G/B | B/A | B/A |

Recommendations may be presented to the user in the form of a table in the printed instructions to the user, as shown above, or, alternatively, by inputting the Daily/Weekly/Monthly Change indications into expression logic, for example, within the code executed by processor 310, which then outputs the relevant recommendation either via text on, for example, display 314, or via a speech synthesized instruction output from speaker 320 or earphones 322.

Figure 8:
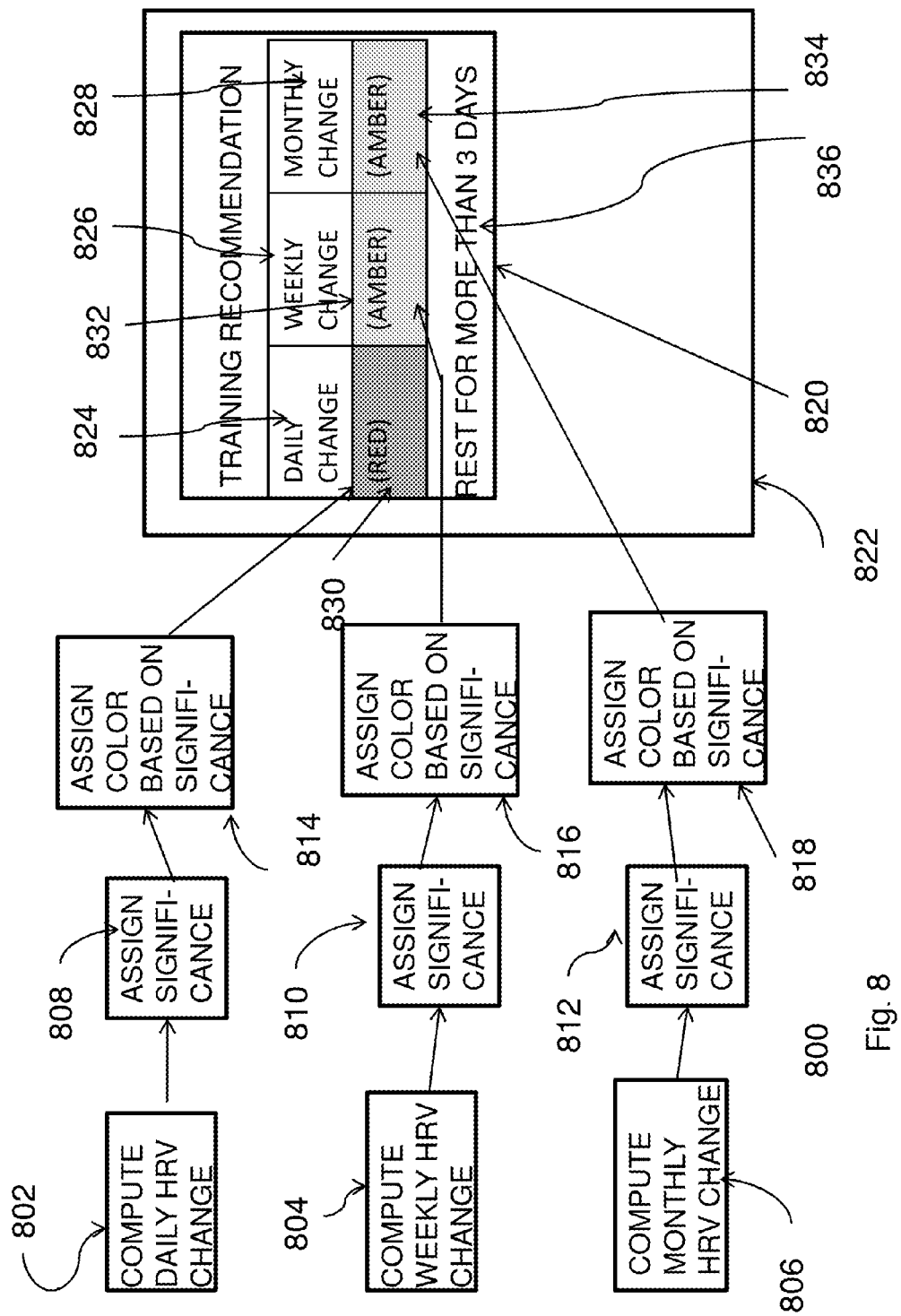
FIG. 8 shows an example of the steps of the computation and display of training recommendations based on HRV measurements.

Referring now to FIG. 8, Daily, Weekly, and Monthly HRV change may be computed, for example, at steps 802-806, and significance may be assigned to these changes at steps 808-812, respectively, for example, as previously described. HRV change and significance value assignment may be realized in hardware and/or software, for example, by software running on CPU 310, special purpose digital hardware, or a combination of software and hardware. Color-coding may be assigned to the significance values assigned to daily change, weekly change, and monthly change at steps 814-818, respectively. Training recommendations may be presented to the user, for example, in the form of color-coded indicators 830-834 of the significance of daily, weekly, and monthly changes in HRV labeled as such by texts 824-828, respectively on display 820 of device 822. For example, using the previously described color code assignments, the daily change may be assigned the value "highly significant negative change" and the indicator 828 may be assigned the color red. The weekly and monthly changes may both be assigned the value "significant negative change" and the color amber, and these colors may be displayed by indicators 832 and 834, respectively, on display 820 of device 822. Based upon the values assigned to the daily, weekly and monthly changes, training recommendations may be presented to the user, for example, as text 836 on a portion of display 820 of device 822. Indicators 830-834 and recommendations 836 may be presented by hardware and/or software, for example, by software running on CPU 310, and display control hardware and a display 820 known in the art.

In some embodiments, the user may input a periodic, for example, daily mood score, using for example, the control panel 224 of device 228. The mood score (which may be based on fatigue, stress or other mood states known in the art) may, for example, comprise a number from 1 to 5, with 1 representing "happiest" and 5 representing "unhappiest". The system may store the daily mood score in a first database (e.g., database 222 in some embodiments). The system may retrieve a set of HRV values from a second database, e.g., database 710 of FIG. 7, which may comprise a portion of the same database used to store the mood scores, e.g., database 222 of FIG. 2. Referring now to FIG. 9, the device, for example, device 228 may display, for example, day names 910 and/or dates 912, mood scores 916, and HRV values 914 simultaneously, for example on display 226, so that the user can correlate her mood with her HRV value. In some embodiments, icons 918 representing mood scores may be displayed instead of or in addition to numerical mood scores 916. For example, an icon 920 representing a "very smiley face" may be displayed, either alone or in close proximity to the number 1, to represent the "happiest mood", a "somewhat smiley face" icon 922 may be displayed, either alone or in combination with the number 2, to represent a somewhat happy mood, a "neutral face" icon 924 (horizontal mouth line) may be displayed, either alone or in combination with the number 3, to represent a neutral (neither happy nor unhappy) mood, a "somewhat frowning face" icon 926 may be displayed, either alone or in combination with the number 4, to represent a "somewhat unhappy" mood, and a "very frowning face" icon 928 may be displayed, either alone or in combination with the number 5, to represent a "very unhappy" mood. The purpose of the mood recording, display, and correlation may be for example to assist the user in diagnosing the onset of overtraining, where the HRV value alone may not provide conclusive enough evidence. It may also assist in the detection of training monotony, independent of HRV value, where too much of the same type of training is being performed.

As opposed to the usual prospective study group statistical approach, The method and system described above introduces the capability to perform self contained measurements, permitting long term longitudinal study of HRV variations within individuals, by taking periodic, for example, daily, measurements for only one individual over the long term.

In some embodiments, a measure of fitness is computed from a set of HRV values compiled over an extended period of time. For example, HRV values compiled on a daily basis may be stored, for example, in database 222 of FIG. 2, for weeks, months, or even years. A first fitness measure may then be computed using, for example, HRV values compiled over a first one-week period. This first fitness measure may then be presented to the user, together with a second fitness measure computed using stored HRV values for a second, later one-week period for example, on display 226 of device 228. The user may then be able to appreciate her relative change in fitness to assess, for example, the success or lack thereof of her training program. The user may also be able to take preventative measures by, for example, consulting her physician, should the difference in presented fitness measures indicate a marked deterioration in fitness.

In another example, the user may be presented with a measure of her fitness on a short term, e.g., daily basis, even though that measure of fitness is computed for an extended period of tune, for example the one-month period preceding the current day.

A measure of a user's relative fitness for an extended time period may be computed by taking the difference between the current average HRV value and the average value stored at an earlier point in time, usually several weeks or months previously, and under comparable conditions e.g., following a rest period of several days, e.g., in database 222, which may, for example, comprise a portion of memory 312. Measures of relative fitness may be computed, for example, by software running on a CPU 310, special purpose digital hardware, or a combination of software and hardware. If the user's fitness at the earlier time point is known (for instance expressed as VO2 peak), then an increase in average HRV is likely to signify an improvement in VO2 peak, and vice versa for a negative change.

In another embodiment, the method and system may provide the functionality of an HRV-based alarm clock. For example, device 110, which may comprise device 228 in some embodiments, may generate an awakening stimulus to user 102 (user 202 in some embodiments) designed to awaken the user when the difference between the HRV index measured while the user is sleeping and the HRV index measured prior to the user falling asleep exceeds a predetermined threshold. In general, generating an awakening stimulus may be realized by a combination of software and/or hardware, for example, generating the stimulus may be controlled by software running on CPU 310 and the stimulus itself may be delivered to the user by means of hardware known in the art. For example, since the increase in the parasympathetic HRV index, that the present invention measures, back towards the rolling average is associated with recovery, the device 110 may be run continuously while the user is asleep in one specific embodiment and an awakening stimulus, for example, a loud sound, may be generated by the device 110 to wake the user up when sufficient recovery has occurred, as indicated by the difference between waking and sleeping HRV index exceeding a predetermined threshold. In calculating the difference between waking and sleeping HRV, the waking HRV value may be stored in, for example, memory 312 or any other suitable storage device. The generation of the loud sound may, for example be controlled by software running on CPU 310 and the generation of the sound itself may be via D/A converter 318 and speaker 320. Alternatively, device 110 may provide a direct stimulus to the user via a wired or wireless link to a transducer (not shown) attached to the user 102. For example, a vibrating transducer around the user's wrist may receive a vibrate command wirelessly from device 110, for example, under the control of software running on CPU 310, and transmitted by modulator 324. This HRV-based alarm clock function may be of special value to people who need to stay awake as much as possible, but still need to function well, e.g., round the world sailors, expedition members, military on assignment, top politicians, business leaders etc., but may also be of value to any user who needs to maximize her productivity while also achieving sufficient recovery after sleep.

In another embodiment, a periodic HRV measurement may be used for management of hypertension and pre-hypertension in individuals. It is known that low and reducing values of parasympathetic HRV can precede either the development, or worsening, of hypertension. It is also known that frequently recommended lifestyle modifications, such as increasing levels of exercise, dietary fruit and vegetables, rest, sleep and relaxation, and reducing body weight, stress, smoking, alcohol and dietary salt all have a significant and often rapid impact on parasympathetic activity which can be reflected in a periodic HRV measurement.

Figure 10:
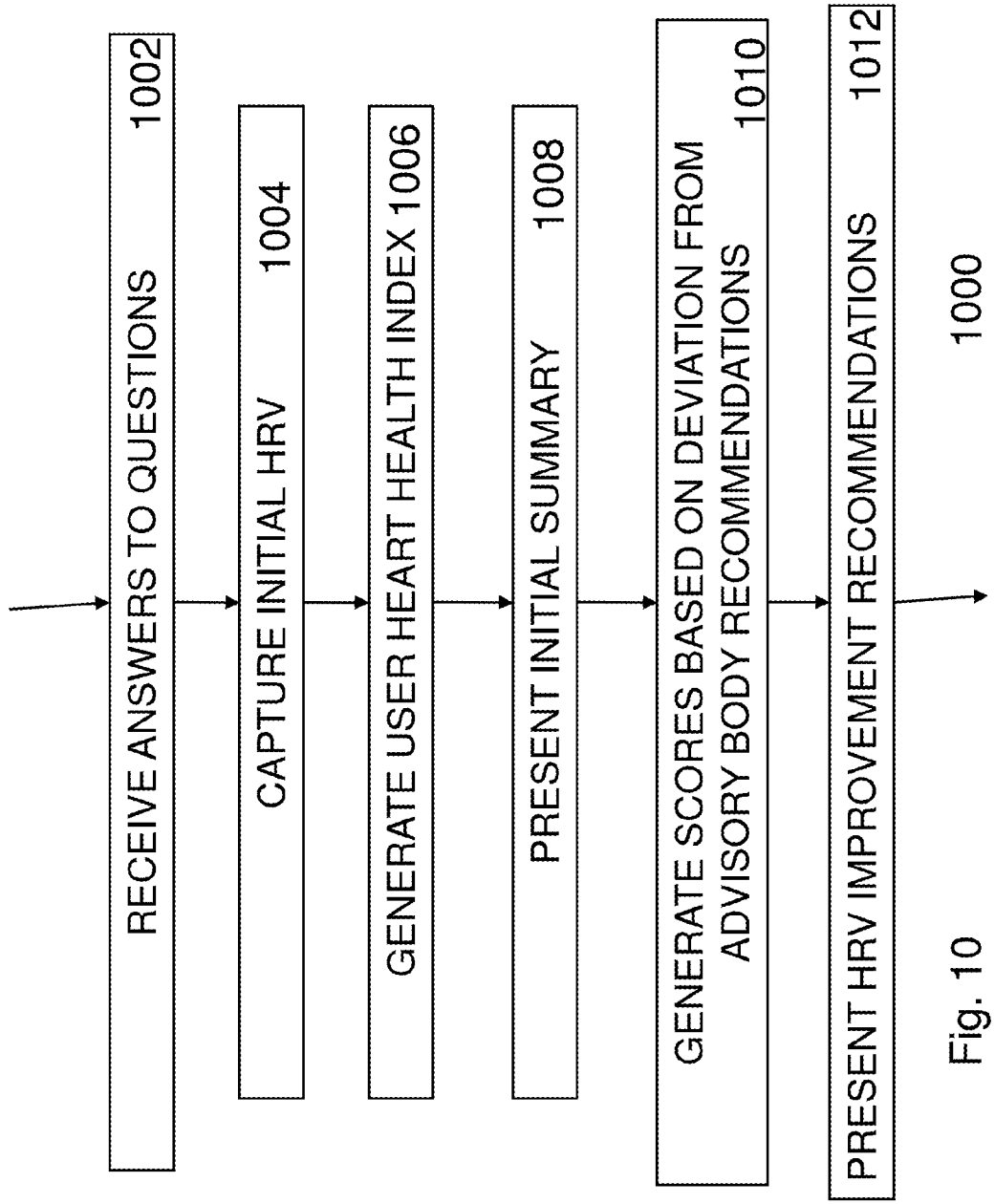
FIG. 10 shows an example of the steps of determining and presenting recommendations regarding the management of hypertension based on HRV measurements.

Referring now to FIG. 10, which may, for example, be partly implemented by CPU 310 executing instructions fetched from a portion of memory 312, at step 1002, in this embodiment, a user may input answers, for example using control panel 224 under the control of software, for example running on CPU 310, in response to a series of personal profile questions, which may be presented to the user for example, on display 226, under the control of software, for example running on CPU 310. As one example, these questions may include:

1. Age
 2. Sex
 3. Body weight
 4. Body Mass Index (or hip-waist size ratio)
 5. Amount of exercise (hrs per week, or TRIMP)
 6. Smoking (cigarettes per day)
 7. Alcohol intake (units per week)
 8. Sleep amount (hrs per night)
 9. Overall stress score
 10. Overall mood score
 11. Family history of heart disease (positive value if either natural parent has a history of cardiovascular disease)
 12. Blood pressure (last known reading)

13. Nutrition (number of fruit and vegetable servings per day)

The answers to these questions may be utilized is as follows:

At step 1004 an initial HRV reading for the user may be captured according to the method described in the preceding paragraphs. At step 1006, a Heart Health Index may be generated by comparing the value of the initial HRV reading against, for example, pre-stored values of norms of HRV in both sexes of the general population within a particular age range that includes the current age of the user. This comparison may be performed by any combination of hardware and software, for example, by software running on CPU 310 and/or special purpose hardware, using techniques known in the art. These HRV norms may be based on data previously published in scientific papers, or may be established by pooling data from many users of the present invention. The HRV norms may be pre-stored, for example, in a portion of memory 312, by downloading under the control of CPU 310, using a wired or wireless interface (not shown in FIG. 3).

At step 1008, an initial summary may be presented to the user, for example, on display 226, indicating the percentile range within which their age and sex normalized HRV reading sits.

At step 1010, for each of the parameters 3-13 in the above list, a score may be generated on, for example, a 5 point scale (from +2 to −2) indicating the better/worse deviation of the answers from recommendations provided by, e.g., the US National Institute of Health Joint National Committee in the 7th report of prevention, detection, evaluation and treatment of high blood pressure, or other public advisory body on cardiovascular health. These scores may be generated by any combination of hardware and software, for example, by software running on CPU 310 and/or special purpose hardware, using techniques known in the art.

At step 1012, a set of recommendations for improvement of the HRV value may be generated and presented to the user, for example on display 226, based on the scores obtained from step 1010. For example, if the user's BMI is greater than 30 then they will be urged to lose weight, and if their exercise score is also low, to include an exercise program whose intensity and frequency may also be prescribed using the method, system and software described in the preceding paragraphs.

The following table shows one example of a recommendation of lifestyle modifications in order to improve HRV reading (and consequently cardiovascular health) that may be presented to the user.

| Parameter | Initial Value | Compared to norm (points) | HRV compared to norm | Recommendation to user |
|---|---|---|---|---|
| Body Mass Index | 30 | −2 | −1 | walk 90 minutes per week |

Overtraining is a potentially serious condition which occasionally affects athletes who are involved in periods of very high intensity training, and typically takes a period ranging between a few days up to several months of complete rest in order to recover.

The medical diagnosis of overtraining is currently performed using symptoms of persistent tiredness, unusually high (or sometimes low) resting heart rate, low mood score, and an inability to perform at normal levels during training or competition. In addition, there has been scientific interest in the use of heart rate variability to increase the robustness of diagnosis, but no definitive method incorporating this variable has yet been proposed.

This diagnosis & cure of overtraining has three main problems in the situation when an athlete presents themselves to a medical professional.

1. It is difficult to distinguish between the above mentioned symptoms of overtraining and those of other illnesses, particularly since overtraining itself often weakens the immune system, allowing the symptoms of secondary infections to manifest themselves.

2. The symptoms of overtraining can be confusing, for instance in one form of overtraining, known as "parasympathetic overtraining", the athlete can present with a low resting heart rate, normally indicative of a well recovered state, yet they are unable to perform at the athletic level expected of them.

3. By the time the athlete presents themself to a medical professional, the overtraining state may be well established, meaning that the athlete will need to be out of action for a substantial period of time while they recover.

A method of detecting overtraining is described hereinafter, based on the following principles:

1. The Polyvagal Theory (1995-2007) of Professor Stephen Porges. Ref: Biological Psychology 74 (2007) 116-143.

2. The time progression of overtraining cardiac markers, particularly resting heart rate (RHR) and parasympathetically mediated respiratory sinus arrhythmia (RSA) HRV, as measured and quantified using the natural logarithm of the RMSSD.

Taking these in turn:

1. The Polyvagal Theory, conceived and usually applied in the field of psychophysiology, proposes that the parasympathetic nervous system of mammals has two distinct branches, originating in different parts of the brain, and carried by different types of nerves to the pacemaking (sinoatrial) region of the heart.

The Polyvagal Theory argues that when an animal's central nervous system is presented with a challenge (which can be either from the animal's environment, or from its own internal organs, or viscera), the autonomic nervous system (in total) of that animal will attempt to deal with the challenge by successively activating branches of the ANS in the following order:

i) Parasympathetic nervous system, with stimulus originating in the Nucleus Ambiguous of the brainstem, carried via myelinated nerves to the heart, and having the impact of reducing heart rate rapidly (1 sec or less) during expiration.

ii) Sympathetic nervous system, carried by unmyelinated nerves, and having the impact of increasing heart rate over a period of several seconds.

iii) Parasympathetic nervous system with stimulus originating in the dorsal motor nucleus, carried via unmyelinated nerves, and having the impact of reducing heart rate over a period of several seconds.

2. The use of a daily (or other frequent periodic) measurement of two variables—resting heart rate (RHR) and a measure of HRV, for example, Ln RMSSD, can be used to separate out the specific states in the above progression according to the following table, where "Normal" refers to a rolling average of recent values (for instance the past 7 days), and "Reduced" or "Increased" refer to the numerical relationship between the current value and the "Normal" value, having passed tests of statistical significance.

| STATE | TIME | Ln RMSSD | RHR |
|---|---|---|---|
| Recovered | 0 | Normal | Normal |
| After training | 1 | Reduced | Normal |
| "Sympathetic" overtrained | 2 | Reduced | Increased |
| "Parasympathetic" overtrained | 3 | Reduced (in a few cases may be normal or even increased) | Decreased |

Figure 11:
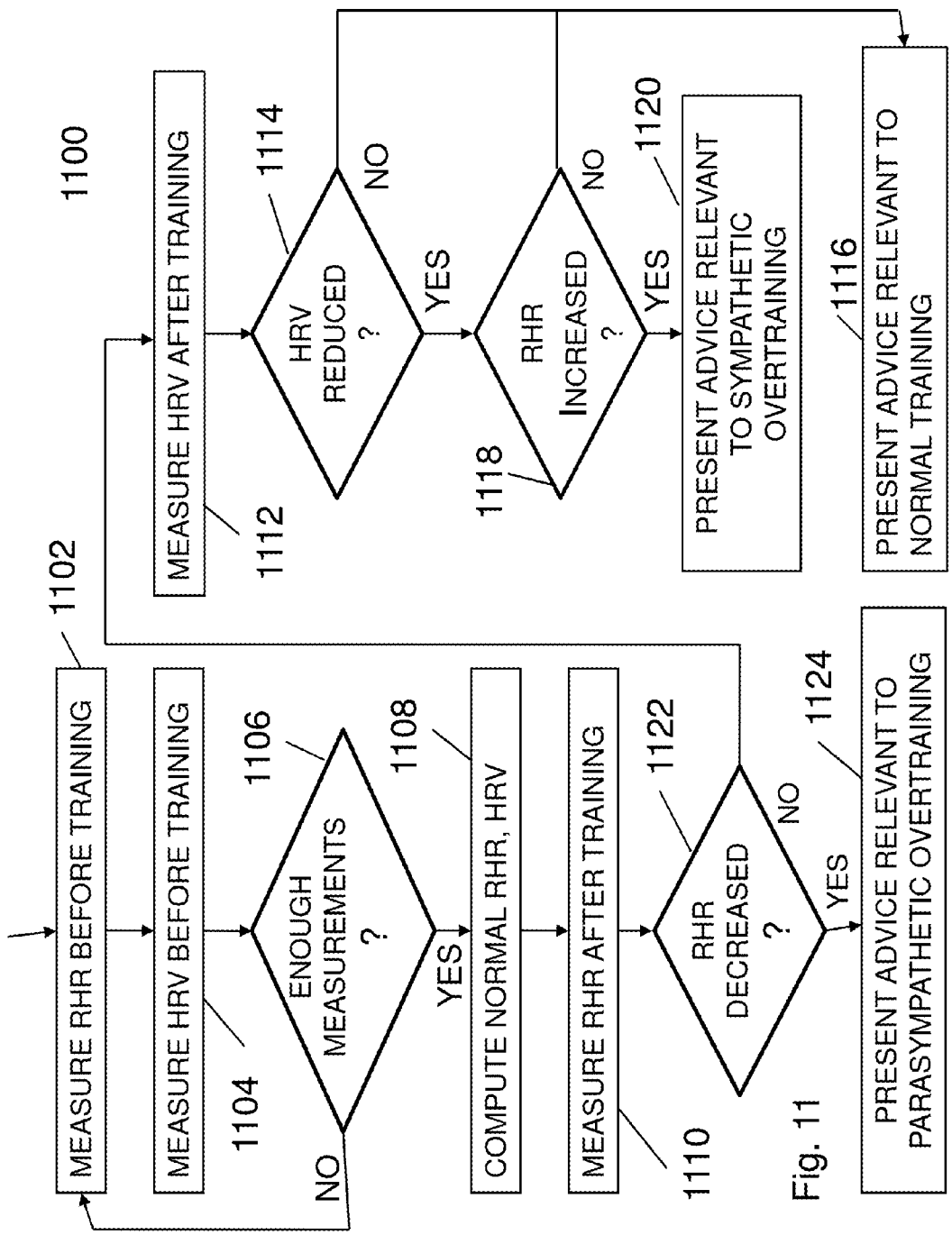
FIG. 11 shows an example of the steps of determining and presenting recommendations relevant to overtraining based on HRV measurements.

In one embodiment, athletic overtraining is measured and ameliorated as described below with reference to FIG. 11. At step 1102, the heart rate of a resting user (Resting Heart Rate or RHR) may be measured before training. This measurement may be performed by any combination of hardware and software, for example, by software running on CPU 310 and/or special purpose counter/timer hardware, such as described in the preceding paragraphs with reference to function 218. At step 1104, HRV may also be measured, for example as Ln RMSSD, computed, for example as the output of block 220. At step 1106, it may be determined, e.g., by software running on CPU 310, whether enough RHR and HRV measurements have been taken to insure that reliable "normal" values, for example average values, of RHR and HRV may be computed by any combination of hardware and software, for example, by software running on CPU 310 and/or special purpose hardware, using techniques known in the art.

If sufficiently reliable values of RHR and HRV are available at step 1108, then RHR may be measured after training at step 1110. At step 1122, it may be determined whether the value of RHR after training is lower than the value of RHR before training by a predetermined amount. If so, then at step 1124, recommendations relevant to parasympathetic overtraining, as described hereinbefore, for example, recommendations on reducing training load or recommendations on resting, may be presented to the user. If, on the other hand, the value of RHR after training is not lower than the value of RHR before training, then at step 1112 the value of HRV after training may be measured. At step 1114 it may be determined whether the value of HRV after training is lower than the value of HRV before training by a predetermined amount. If not, recommendations relevant to normal training, as described hereinbefore, for example, with reference to FIG. 8, may be presented to the user at step 1116. If, on the other hand, HRV is reduced, then at step 1118 it may be determined if the value of RHR after training is higher than the value of RHR before training. If so, then at step 1120, recommendations relevant to sympathetic overtraining, for example, recommendations on reducing training load or recommendations on resting, may be presented to the user. If, on the other hand, the value of RHR after training is not higher than the value of RHR before training, then recommendations relevant to normal training may be presented to the user at step 1116.

Thus, it may be possible to provide an unambiguous diagnosis of different states of overtraining, and furthermore, by identifying the progression, avoid the development of the most dangerous form known as Parasympathetic Overtraining by reducing training load and building in rest and recovery at a much earlier stage.

In another embodiment, the exercise dose for patients with heart failure may be prescribed. Regular aerobic exercise in heart failure patients has been established as a beneficial lifestyle modification that could significantly improve their prognosis and decrease costs associated with chronic care. A conundrum exists between the need to carry out exercise at sufficient intensity and duration to bring about beneficial changes while taking care not to overload patients whose tolerance for physiological stress may be very low. Vagal efferent activity has been shown to be strongly negatively correlated with short term overload and positively with beneficial longer term cardioprotective adaptations. It can be measured non-invasively by examining respiration mediated variation in beat to beat intervals (RSA).

The target population of heart failure (HF) patients present additional challenges compared to healthy subjects for several reasons:

1. The RR intervals of HF patients are more likely to possess sinus arrythmia of non-respiratory origin than healthy subjects. Obtaining sufficient consistency in daily measurement will necessitate more advanced forms of automatic beat interval screening, removal and/or correction than are currently used in a healthy population. Knowledge of the current phase in the paced breathing cycle can be used to determine the likelihood of a measured beat interval value being correct.

During inhalation, as identified at step 406, the autonomic nervous system (parasympathetic branch) of the user withdraws stimulation, with the consequence that the R-R interval is shortened. Since the method, for example as previously described with reference to FIGS. 1 and 2, includes a controlled breathing pattern, beats that are longer than the average R-R interval (which may be calculated over one or more complete breath cycles) during inhalation may be identified at step 410 and excluded at step 414. In practice an additional margin, shown as x in step 410, may be included to allow for the fact that the user's breathing may not be perfectly synchronized with, e.g., the lung animation 106 of FIG. 1.

During exhalation, as identified as not-inhalation at step 406, a maximum allowed difference between adjacent R-R intervals can also be predicted by knowing the average R-R interval taken over one or more complete breath cycles during the measurement. This is possible because the parasympathetic-sympathetic balance also controls the standing pulse rate. A formula has been determined empirically from observations on multiple users, whereby the maximum permitted R-R interval difference may be related to the square of the mean R-R interval divided by a constant, for example 12000. Therefore, R-R intervals not conforming to:

$$\text{Max allowed adjacent } R\text{-}R \text{ interval difference} = (\text{mean } R\text{-}R \text{ interval})^2/12000$$

may be identified at step 412 and excluded at step 414. As previously described, the mean R-R interval calculation may commence earlier than the HRV calculation during the measurement sequence so that all R-R intervals considered for inclusion in the HRV calculation may be adequately assessed for validity. Intervals not identified for exclusion according to the preceding criteria are included in the HRV calculations, e.g., the RMSSD calculations of processor 220, at step 416.

2. Heart failure patients frequently suffer from atrial fibrillation (AF), and while it has been shown in the literature that vagal modulation is still apparent in the RR interval, the measurement basis may be significantly different to that of the same patient not suffering from AF. Therefore, intrapatient comparisons will have to be performed in order to compare HRV values with and without AF and establish normative/conversion values in the device.

In the case that a user has a temporarily irregular heart rhythm, such as palpitations, Atrial Fibrillation, or SupraVentricular Tachycardia, this may lead to a number of excluded intervals according to the set of rules outlined in the previous paragraphs. In case the number of such excluded beats exceeds a predefined threshold, e.g., 5, during the measurement sequence, then the measurement will be terminated and the user informed of the reason, and instructed to retake the measurement after some period of time. This is in order to prevent incorrect readings from contaminating the calculation of longitudinal averages and other statistical measures upon which color codes and recommendations are based.

3. Cardiac patients have significantly decreased HRV compared to healthy controls, and vagally modulated HRV is lower even for healthy controls in the standing position Patients with advanced HF may also have trouble standing, so it may be that either sitting or supine positions are best for performing the daily test. This is not likely to result in saturation of parasympathetic stimulus, as it might do for an athletic individual.

4. A paced breathing pattern of long duration (example 8 seconds) suitable for healthy subjects may not be applicable to patients with dyspnea (shortage of breath), therefore it may be that a paced breathing pattern with shorter periods of controlled inhalation, expiration and holding times needs to be used for HF patients. It is preferable to have the expiration as the longest phase of the breathing pattern, so for example an inhalation period of 2 seconds, followed by expiration of 3 seconds may be used.

5. Heart failure patients will have a lower tolerance for homeostasis disturbance resulting from exercise, therefore suitable thresholds for daily exercise recommendation may need to be based on multiple algorithmic rules reflecting maximum allowable inter day changes in vagal HRV. Recovery times will also be longer than in healthy subjects, and these also need to be taken into account. In some embodiments an individualized exercise prescription may be conveyed to the user either via text on the screen of the device, or perhaps voice synthesis. This needs to be demanding enough to stimulate supercompensation with associated improvement in autonomic function, but not so demanding that it causes increased risk to the patient.

6. Heart failure patients will have lower tolerance to exertion during exercise than healthy subjects. It is known that parasympathetic stimulus is withdrawn as exercise intensity increases, and also known that parasympathetic activity is cardioprotective against potentially lethal arrhythmia, to which heart failure patients may be susceptible. For this reason it is desirable that parasympathetic activity not fall below a safe level. This embodiment can therefore also be used in a continuous measuring mode, whereby both the HRV and heart rate (HR) are calculated, for example, every 10 seconds. As the user increases their exercise intensity from rest (exercise types may include walking, cycling, jogging, rowing machine etc), their heart rate will increase in order to pump more blood to their working muscles, and their HRV will decrease, as parasympathetic stimulus is withdrawn. IF the values of both parameters from successive measurements are compared, a parasympathetic withdrawal index (PWI) may be calculated as follows:

$$PWI=(HRV1-HRV2)/(HR2-HR1)$$

When PWI is less than a threshold value, a sonic and/or visual alarm may be given to the user, urging them to reduce exercise intensity until the PWI once again exceeds the safe threshold.

Figure 12:
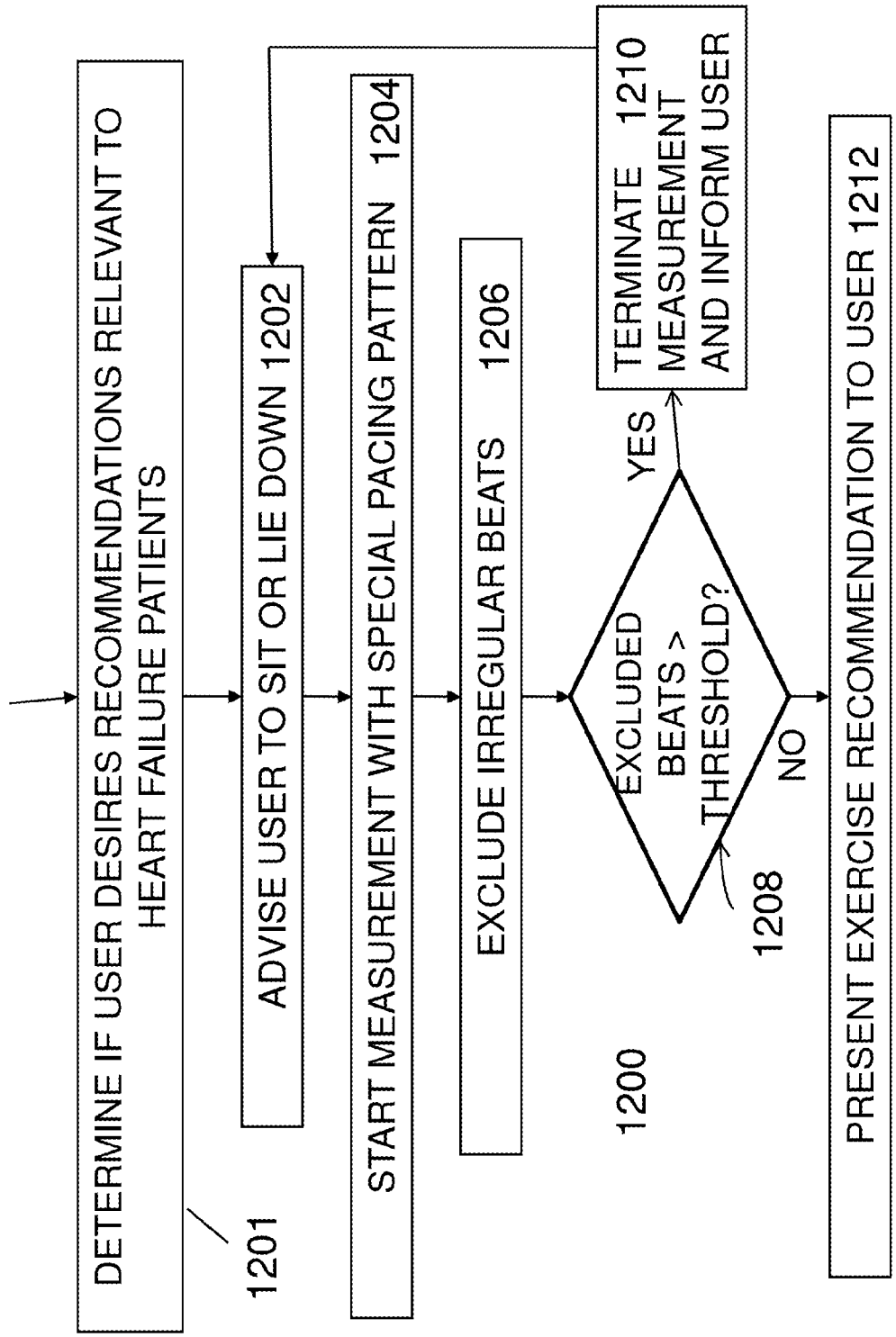
FIG. 12 shows an example of the steps determining and presenting exercise recommendations to users suffering from heart failure based on HRV measurements.

In one embodiment, HRV for a user with heart failure is measured and exercise is recommended to improve the user's HRV measure as described below with reference to FIG. 12. At step 1201, it may be determined that the user wants recommendations relevant to heart failure patients by, for example, presenting an option to select this response to the user on display 226, under the control of software running on CPU 310, and/or using audible output via speaker 320 or earphones 322. For the reason described in the preceding paragraphs, at step 1202, the user may be instructed to sit or lie down, for example, via a message on display 226, under the control of software running on CPU 310, and/or using audible output via speaker 320 or earphones 322. At step 1204, HRV measurement may be started using the aforementioned specially-paced breathing pattern, for example, an inhalation period of 2 seconds, followed by expiration period of 3 seconds may be used. Irregular beats may be excluded using the method described in the preceding paragraphs at step 1206. At step 1208, excluded irregular beats may be compared to a predetermined threshold, and if this threshold is exceeded, at step 1210 the measurement may be terminated, for example under the control of software running on CPU 310, and the user informed, for example, that the measurement could not be reliably taken and must be retaken some time later. If the irregular beat threshold is not exceeded, then at step 1212 the user may be presented with an exercise recommendation appropriate to a user with heart failure.

7. Centralized data collection should be performed more frequently than for healthy controls due to the increased risks that cardiac patients carry. In this embodiment, the device 110 may have the ability to communicate, for example, using standard protocols such as WiFi, in the case where device 110 is a PC, or GSM, in the case where device 110 is a cell phone, the HRV reading and other databases to a central server (not shown) capable of storing and analyzing the results, and alerting a medical expert when needed, for instance if a declining trend of HRV is seen over an example period of 3 days or more.

Figure 13:
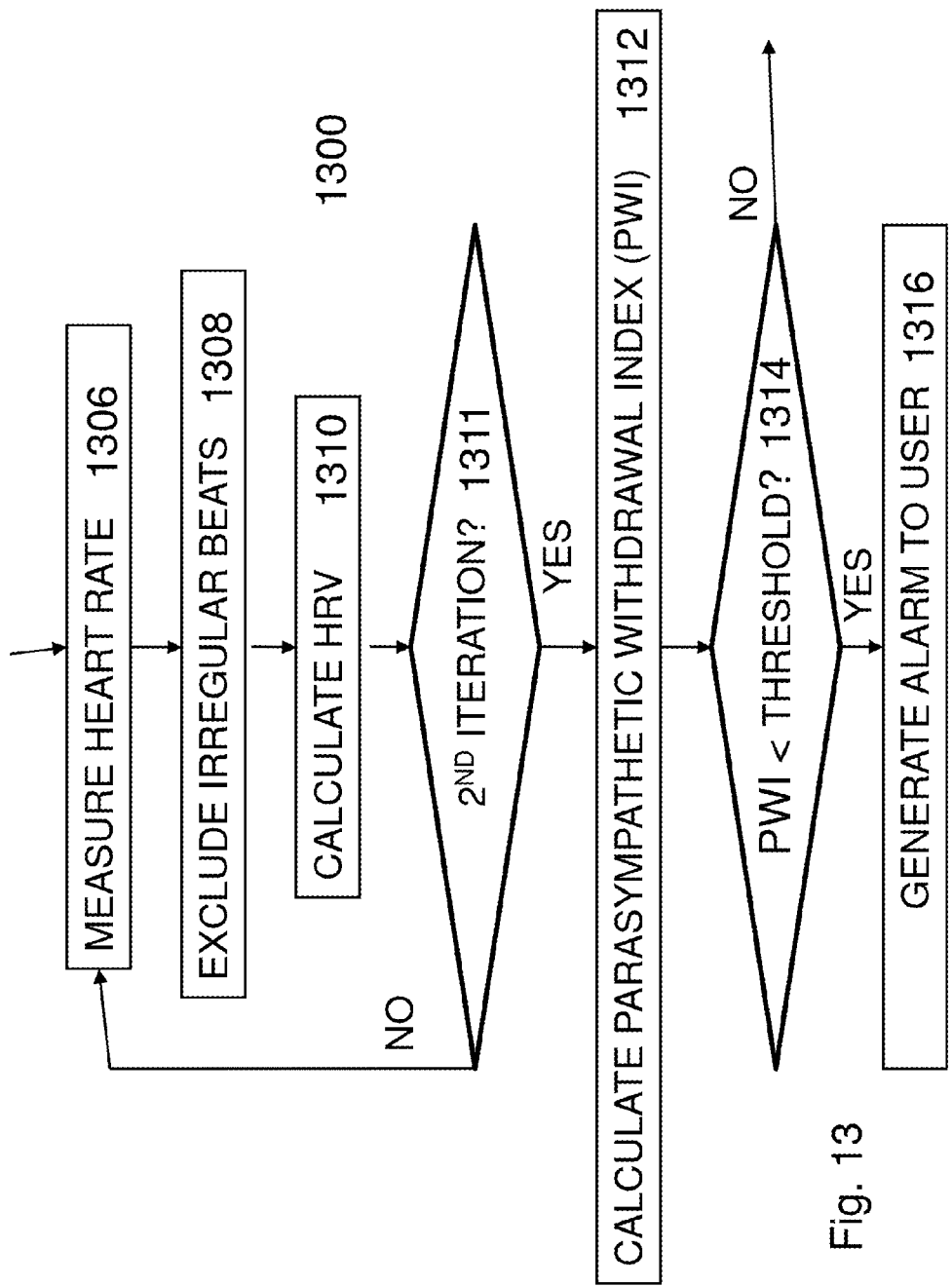
FIG. 13 shows an example of the steps of monitoring and alerting a user to a potentially serious decline in parasympathetic activity based or HRV measurements.

Referring now to FIG. 13, in another embodiment, HRV for users with heart failure is measured continuously, as described in the preceding paragraphs. Prior to starting the flow of FIG. 13, it may be decided whether an HRV measurement should be started or re-started, based on, for example, input from the user to start or stop the continuous measurement mode of operation of, for example, device 228 and whether a timer, for example, a 10 second timer (not shown), has expired. If the user has decided to start a new measurement, or in the case of continuous measurements, the user has not stopped the continuous measurements, then at the start of each measurement interval, for example, every 10 seconds, a new value of heart rate may be measured at step 1306. Irregular beats may be excluded, as described in the preceding paragraphs, at step 1308, and a new value of heart rate variability may be calculated at step 1310. At step 1312, a new value of PWI may be calculated, as described in the preceding paragraphs, by hardware and/or software, for example, by software running on a digital CPU, special purpose hardware, or a combination of software and hardware. If PWI is less than a predetermined threshold, then at step 1314, an alarm may be generated to the user. If PWI is not less than the predetermined threshold, then no alarm is generated to the user. The alarm may be generated by a combination of hardware and software, for example, the alarm may be initiated by software running on CPU 310 and an alarm sound generated by D/A converter 318 and speaker 320. Alternatively, device 110 may be caused to vibrate by a transducer (not shown in the figures) controlled by software running on CPU 310. Alternatively to or in conjunction with device 110 generating an alarm sound or vibrating, a prominent message, for example, a flashing alarm message, may be generated on display 108 under the control of software running on CPU 310.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention as claimed.

The embodiments of the present invention may be implemented with any combination of hardware and software. If implemented as a computer-implemented apparatus, the present invention is implemented using means for performing all of the steps and functions described above.

The embodiments of the present disclosure can be included in an article of manufacture (e.g., one or more computer program products) having, for instance, computer useable or computer readable media. The media has embodied therein, for instance, computer readable program code means, including computer-executable instructions, for providing and facilitating the mechanisms of the embodiments of the present disclosure. The article of manufacture can be included as part of a computer system or sold separately.

While specific embodiments have been described in detail in the foregoing detailed description and illustrated in the accompanying drawings, it will be appreciated by those skilled in the art that various modifications and alternatives to those details could be developed in light of the overall teachings of the disclosure and the broad inventive concepts thereof. It is understood, therefore, that the scope of the present invention is not limited to the particular examples and implementations disclosed herein, but is intended to cover modifications within the spirit and scope thereof as defined by the appended claims and any and all equivalents thereof.

What is claimed is:

1. A method of measuring heart rate variability of a user, comprising:
   displaying an animation that indicates to the user when to breathe in and breathe out;
   receiving a signal from a sensor responsive to the user's heart beat while the user breathes in and out as indicated by the animation;
   processing the received signal to determine heart beat intervals of the user;
   calculating a measure of heart rate variability of the user from the processed heart beat intervals; and
   excluding irregular heart beat intervals from the calculation of heart rate variability.

2. The method of claim 1, further comprising:
   generating a first sound that indicates to the user when to breathe in; and
   generating a second sound that indicates to the user when to breathe out.

3. The method of claim 1, further comprising generating synthesized audible output to the user selected from the group comprising instructions on how to place the sensor, instructions on when to breathe in, and instructions on when to breathe out.

4. The method of claim 1, further comprising:
   inputting by the user on a periodic basis a value of mood;
   storing the periodic mood values in a first database;
   storing periodic heart rate variability values in a second database;
   retrieving from the first database a set of periodic mood values recorded over a predetermined period of time;
   retrieving from the second database a set of periodic heart rate variability values for corresponding to a period of time substantially equal to the predetermined period of time; and
   presenting the set of mood values and the set of heart rate variability values to the user substantially simultaneously.

5. The method of claim 4, wherein the presented mood values are displayed as icons.

6. The method of claim 1, further comprising:
   storing a number of successively measured heart rate variability measures in a database;
   retrieving from the database a first set of heart rate variability measures stored over a first predetermined extended period of time;
   retrieving from the database a second set of heart rate variability measures stored over a second predetermined extended period of time subsequent to the first extended period of time; and
   computing a measure of fitness of the user based on the first set of retrieved heart rate variability measures and the second set of retrieved heart rate variability measures.

7. The method of claim 6, further comprising presenting successive instances of the measure of fitness to the user on a regular basis.

8. The method of claim 6, further comprising:
   presenting to the user a first measure of fitness computed for a first period of time; and
   presenting to the user, at substantially the same time, a second measure of fitness computed for a second period of time substantially different from the first period of time.

9. The method of claim 1, further comprising:
   presenting to the user a set of personal profile questions including at least age and sex;
   inputting from the user answers to the questions;
   capturing an initial heart rate variability measure;
   comparing the initial heart rate variability measure to heart rate variability norms appropriate to the age and sex of the user;
   presenting to the user the result of the comparison;
   generating scores based on the deviation of the answers from corresponding values recommended by at least one advisory body on cardiovascular health; and
   presenting based on the scores at least one recommendation for improving the heart rate variability measure of the user.

10. The method of claim 1, further comprising:
    measuring resting heart rate and heart rate variability of the user a number of times sufficient to compute a valid normal value of resting heart rate and a valid normal value of heart rate variability before the user engages in physical training;
    computing the valid normal value of resting heart rate and the valid normal value of heart rate variability of the user;
    measuring resting heart rate after the user engages in physical training;
    presenting at least one recommendation to the user relevant to parasympathetic overtraining if the resting heart rate of the user measured after training is less than the normal resting heart rate of the user;
    measuring heart rate variability after the user engages in physical training if the resting heart rate of the user after physical training is not less than the normal resting heart rate of the user;
    presenting at least one recommendation to the user relevant to sympathetic overtraining if the heart rate variability of the user measured after training is less than the normal resting heart rate variability of the user and the resting heart rate of the user measured after training is greater than the normal resting heart rate of the user;

presenting at least one recommendation to the user relevant to normal training if the heart rate variability of the user measured after training is not less than the normal resting heart rate variability of the user; and presenting at least one recommendation to the user relevant to normal training if the heart rate variability of the user measured after training is less than the normal heart rate variability of the user and the resting heart rate of the user measured after training is not greater than the normal resting heart rate of the user.

11. A method of measuring heart rate variability of a user, comprising:

displaying an animation that indicates to the user when to breathe in and breathe out;

receiving a signal from a sensor responsive to the user's heart beat while the user breathes in and out as indicated by the animation;

processing the received signal to determine heart beat intervals of the user;

calculating a measure of heart rate variability of the user from the processed heart beat intervals;

inputting by the user on a periodic basis a value of training load;

storing the periodic training load values in a first database;

storing periodic heart rate variability measures in a second database;

retrieving from the first database a set of periodic training load values input over a predetermined period of time;

computing a histogram of the retrieved periodic training load values;

retrieving from the second database a set of periodic heart rate variability measures corresponding to a period of time substantially equal to the predetermined period of time; and presenting the histogram and the set of heart rate variability measures to the user substantially simultaneously.

12. A method of measuring heart rate variability of a user, comprising:

displaying an animation that indicates to the user when to breathe in and breathe out;

receiving a signal from a sensor responsive to the user's heart beat while the user breathes in and out as indicated by the animation;

processing the received signal to determine heart beat intervals of the user;

calculating a measure of heart rate variability of the user from the processed heart beat intervals;

computing a first measure of short term change of the heart rate variability measure;

computing a second measure of medium term change of the heart rate variability measure;

computing a third measure of long term change of the heart rate variability measure;

assigning to the first change measure a first value of significance;

assigning to the second change measure a second value of significance;

assigning to the third change measure a third value of significance; and presenting to the user at substantially the same time indicators of the first value of significance and the second value of significance and the third value of significance.

13. The method of claim 12, further comprising presenting recommendations to the user based upon the first value of significance and the second value of significance and the third value of significance.

14. A method of measuring heart rate variability of a user, comprising:

receiving a signal from a sensor responsive to the user's heart beat;

processing the received signal to determine heart beat intervals of the user;

calculating a measure of heart rate variability of the user from the processed heart beat intervals, wherein the measure of heart rate variability comprises the RMSSD of the processed heart beat intervals;

determining a logarithm of the RMSSD multiplied by a scale factor; and presenting to the user at least one heart-rate-variability-related datum as the logarithm of the RMSSD multiplied by the scale factor.

15. The method of claim 14, wherein the logarithm is the natural logarithm and the scale factor is 20.

16. A method of measuring heart rate variability of a user, comprising:

displaying an animation that indicates to the user when to breathe in and breathe out;

receiving a signal from a sensor responsive to the user's heart beat while the user breathes in and out as indicated by the animation;

processing the received signal to determine heart beat intervals of the user;

calculating a measure of heart rate variability of the user from the processed heart beat intervals;

determining if the user desires recommendations relevant to heart failure patients;

instructing the user to sit or lie down;

wherein displaying the animation that indicates to the user when to breathe in and breathe out comprises indicating to the user to breathe in more quickly and breathe out more quickly than would be the indication to a user who does not suffer from heart failure;

excluding irregular beats from the heart rate variability measurement;

computing the number of excluded beats over a predetermined period of time;

terminating the heart rate variability measurement if the number of excluded beats exceeds a predetermined threshold; and presenting at least one exercise recommendation appropriate to the user based on the measure of heart rate variability if the number of excluded beats does not exceed the predetermined threshold.

17. A method of measuring heart rate variability of a user, comprising:

displaying an animation that indicates to the user when to breathe in and breathe out;

receiving a signal from a sensor responsive to the user's heart beat while the user breathes in and out as indicated by the animation;

processing the received signal to determine heart beat intervals of the user;

calculating a measure of heart rate variability of the user from the processed heart beat intervals;

processing the received signal by excluding irregular intervals from the heart beat intervals of the user;

calculating heart rate from the processed heart beat intervals;

calculating a Parasympathetic Withdrawal Index using the current value of the heart rate and a prior value of the heart rate and the current value of the heart rate variability measure and a prior value of the heart rate variability measure; and generating an alarm to the user if the Parasympathetic Withdrawal Index is less than a predetermined threshold.

18. A method of measuring heart rate variability of a user, comprising:
instructing the user to breathe in and breathe out at predetermined times;
receiving a signal from a sensor responsive to the heart beat of the user while the user breathes in and out as instructed;
processing the received signal to determine heart beat intervals; and
calculating a measure of heart rate variability from the processed heart beat intervals using a time domain processing method,
wherein the time domain processing method is selected from the group comprising RMSSD, pNN50, and SD1 cluster Poincare plot.

19. A system for measuring heart rate variability of a user comprising:
means for displaying an animation that indicates to the user when to breathe in and breathe out;
means for receiving a signal from a sensor responsive to the user's heartbeat while the user breathes in and out as indicated by the animation;
means for processing the received signal to determine heart beat intervals of the user;
means for calculating a measure of heart rate variability of the user from the processed heart beat intervals; and
means for excluding irregular heart beat intervals from the calculation of heart rate variability.

20. A computer software product embodied in a non-transitory computer-readable physical medium comprising coded instructions for executing a computer process in a digital processor, which computer process generates a measure of heart rate variability, the computer process comprising:
managing display of an animation that indicates to a user when to breathe in and breathe out;
inputting processed heart beat intervals;
wherein the processed heart beat intervals are output by a signal processing means and an input of the signal processing means comprises a signal received by a receiving means from a sensor responsive to the user's heartbeat while the user breathes in and out as indicated by the animation;
calculating a measure of heart rate variability of the user from the processed heart beat intervals; and
executing at least a portion of the signal processing means.

21. A computer software product embodied in a non-transitory computer-readable physical medium comprising coded instructions for executing a computer process in a digital processor, which computer process generates a measure of heart rate variability, the computer process comprising:
managing display of an animation that indicates to a user when to breathe in and breathe out;
inputting processed heart beat intervals;
wherein the processed heart beat intervals are output by a signal processing means and an input of the signal processing means comprises a signal received by a receiving means from a sensor responsive to the user's heartbeat while the user breathes in and out as indicated by the animation;
calculating a measure of heart rate variability of the user from the processed heart beat intervals; and
executing at least a portion of the receiving means.

22. A computer software product embodied in a non-transitory computer-readable physical medium comprising coded instructions for executing a computer process in a digital processor, which computer process generates a measure of heart rate variability, the computer process comprising:
managing display of an animation that indicates to a user when to breathe in and breathe out;
inputting processed heart beat intervals;
wherein the processed heart beat intervals are output by a signal processing means and an input of the signal processing means comprises a signal received by a receiving means from a sensor responsive to the user's heartbeat while the user breathes in and out as indicated by the animation;
calculating a measure of heart rate variability of the user from the processed heart beat intervals;
managing generation of a first sound that indicates to the user when to breathe in; and
managing generation of a second sound that indicates to the user when to breathe out.

23. A computer software product embodied in a non-transitory computer-readable physical medium comprising coded instructions for executing a computer process in a digital processor, which computer process generates a measure of heart rate variability, the computer process comprising:
managing display of an animation that indicates to a user when to breathe in and breathe out;
inputting processed heart beat intervals;
wherein the processed heart beat intervals are output by a signal processing means and an input of the signal processing means comprises a signal received by a receiving means from a sensor responsive to the user's heartbeat while the user breathes in and out as indicated by the animation;
calculating a measure of heart rate variability of the user from the processed heart beat intervals; and
excluding irregular heart beat intervals from the calculation of heart rate variability.

24. The computer process of claim 23, further comprising managing generation of synthesized audible output to the user selected from the group comprising instructions on how to place the sensor, instructions on when to breathe in, and instructions on when to breathe out.

25. The computer process of claim 23, further comprising:
managing inputting by the user on a periodic basis a value of mood;
storing the periodic mood values in a first database;
storing periodic heart rate variability values in a second database;
retrieving from the first database a set of periodic mood values recorded over a predetermined period of time;
retrieving from the second database a set of periodic heart rate variability values corresponding to a period of time substantially equal to the predetermined period of time; and
managing presenting the set of mood values and the set of heart rate variability values to the user substantially simultaneously.

26. The computer process of claim 25, wherein the presented mood values are displayed as icons.

27. The computer process according to claim 23, further comprising:
storing a number of successively measured heart rate variability measures in a database;

retrieving from the database a first set of heart rate variability measures stored over a first predetermined extended period of time;

retrieving from the database a second set of heart rate variability measures stored over a second predetermined extended period of time subsequent to the first extended period of time; and computing a measure of fitness of the user based on the first set of retrieved heart rate variability measures and the second set of retrieved heart rate variability measures.

28. The computer process of claim 27, further comprising managing presenting successive instances of the measure of fitness to the user on a regular basis.

29. The computer process of claim 27, further comprising:

managing presenting to the user a first measure of fitness computed for a first period of time; and managing presenting to the user, at substantially the same time, a second measure of fitness computed for a second period of time substantially different from the first period of time.

30. The computer process of claim 23, further comprising:

managing presenting to the user a set of personal profile questions including at least age and sex;

managing inputting from the user answers to the questions;

managing capturing an initial heart rate variability measure;

comparing the initial heart rate variability measure to heart rate variability norms appropriate to the age and sex of the user;

managing presenting to the user the result of the comparison;

generating scores based on the deviation of the answers from corresponding values recommended by at least one advisory body on cardiovascular health; and managing presenting based on the scores at least one recommendation for improving the heart rate variability measure of the user.

31. The computer process of claim 23, further comprising:

managing measuring resting heart rate and heart rate variability of the user a number of times sufficient to compute a valid normal value of resting heart rate and a valid normal value of heart rate variability before the user engages in physical training;

computing the valid normal value of resting heart rate and the valid normal value of heart rate variability of the user;

managing measuring resting heart rate after the user engages in physical training;

managing presenting at least one recommendation to the user relevant to parasympathetic overtraining if the resting heart rate of the user measured after training is less than the normal resting heart rate of the user;

managing measuring heart rate variability after the user engages in physical training if the resting heart rate of the user after physical training is not less than the normal resting heart rate of the user;

managing presenting at least one recommendation to the user relevant to sympathetic overtraining if the heart rate variability of the user measured after training is less than the normal resting heart rate variability of the user and the resting heart rate of the user measured after training is greater than the normal resting heart rate of the user;

managing presenting at least one recommendation to the user relevant to normal training if the heart rate variability of the user measured after training is not less than the normal resting heart rate variability of the user; and managing presenting at least one recommendation to the user relevant to normal training if the heart rate variability of the user measured after training is less than the normal heart rate variability of the user and the resting heart rate of the user measured after training is not greater than the normal resting heart rate of the user.

32. A computer software product embodied in a non-transitory computer-readable physical medium comprising coded instructions for executing a computer process in a digital processor, which computer process generates a measure of heart rate variability, the computer process comprising:

managing display of an animation that indicates to a user when to breathe in and breathe out;

inputting processed heart beat intervals;

wherein the processed heart beat intervals are output by a signal processing means and an input of the signal processing means comprises a signal received by a receiving means from a sensor responsive to the user's heartbeat while the user breathes in and out as indicated by the animation;

calculating a measure of heart rate variability of the user from the processed heart beat intervals;

managing inputting by the user on a periodic basis a value of training load;

storing the periodic training load values in a first database;

storing periodic heart rate variability measures in a second database;

retrieving from the first database a set of periodic training load values input over a predetermined period of time;

computing a histogram of the retrieved periodic training load values;

retrieving from the second database a set of periodic heart rate variability measures corresponding to a period of time substantially equal to the predetermined period of time; and managing presenting the histogram and the set of heart rate variability measures to the user substantially simultaneously.

33. A computer software product embodied in a non-transitory computer-readable physical medium comprising coded instructions for executing a computer process in a digital processor, which computer process generates a measure of heart rate variability, the computer process comprising:

managing display of an animation that indicates to a user when to breathe in and breathe out;

inputting processed heart beat intervals;

wherein the processed heart beat intervals are output by a signal processing means and an input of the signal processing means comprises a signal received by a receiving means from a sensor responsive to the user's heartbeat while the user breathes in and out as indicated by the animation;

calculating a measure of heart rate variability of the user from the processed heart beat intervals;

computing a first measure of short term change of the heart rate variability measure;

computing a second measure of medium term change of the heart rate variability measure;

computing a third measure of long term change of the heart rate variability measure;

assigning to the first change measure a first value of significance;

assigning to the second change measure a second value of significance;

assigning to the third change measure a third value of significance; and managing presenting to the user at substantially the same time indicators of the first value of significance and the second value of significance and the third value of significance.

34. The computer process of claim 33, further comprising managing presenting recommendations to the user based upon the first value of significance and the second value of significance and the third value of significance.

35. A computer software product embodied in a non-transitory computer-readable physical medium comprising coded instructions for executing a computer process in a digital processor, which computer process generates a measure of heart rate variability, the computer process comprising:
inputting processed heart beat intervals;
wherein the processed heart beat intervals are output by a signal processing means and an input of the signal processing means comprises a signal received by a receiving means from a sensor responsive to the user's heartbeat;
calculating a measure of heart rate variability of the user from the processed heart beat intervals, the measure of heart rate variability comprises the RMSSD of the processed heart beat intervals;
determining a logarithm of the RMSSD multiplied by a scale factor; and
presenting to the user at least one heart-rate-variability-related datum as the logarithm of the RMSSD multiplied by the scale factor.

36. The computer process according to claim 35, wherein the logarithm is the natural logarithm and the scale factor is 20.

37. A computer software product embodied in a non-transitory computer-readable physical medium comprising coded instructions for executing a computer process in a digital processor, which computer process generates a measure of heart rate variability, the computer process comprising:
managing display of an animation that indicates to a user when to breathe in and breathe out;
inputting processed heart beat intervals;
wherein the processed heart beat intervals are output by a signal processing means and an input of the signal processing means comprises a signal received by a receiving means from a sensor responsive to the user's heartbeat while the user breathes in and out as indicated by the animation;
calculating a measure of heart rate variability of the user from the processed heart beat intervals;
managing determining if the user desires recommendations relevant to heart failure patients;
managing instructing the user to sit or lie down;
wherein displaying the animation that indicates to the user when to breathe in and breathe out comprises indicating to the user to breathe in more quickly and breathe out more quickly than would be the indication to a user who does not suffer from heart failure;
managing excluding irregular beats from the heart rate variability measurement;
computing the number of excluded beats over a predetermined period of time;
managing terminating the heart rate variability measurement if the number of excluded beats exceeds a predetermined threshold; and
managing presenting at least one exercise recommendation appropriate to the user based on the measure of heart rate variability if the number of excluded beats does not exceed the predetermined threshold.

38. A computer software product embodied in a non-transitory computer-readable physical medium comprising coded instructions for executing a computer process in a digital processor, which computer process generates a measure of heart rate variability, the computer process comprising:
managing display of an animation that indicates to a user when to breathe in and breathe out;
inputting processed heart beat intervals;
wherein the processed heart beat intervals are output by a signal processing means and an input of the signal processing means comprises a signal received by a receiving means from a sensor responsive to the user's heartbeat while the user breathes in and out as indicated by the animation;
calculating a measure of heart rate variability of the user from the processed heart beat intervals;
managing processing the received signal by excluding irregular intervals from the heart beat intervals of the user;
calculating heart rate from the processed heart beat intervals;
calculating a Parasympathetic Withdrawal Index using the current value of the heart rate and a prior value of the heart rate and the current value of the heart rate variability measure and a prior value of the heart rate variability measure; and
managing generating an alarm to the user if the Parasympathetic Withdrawal Index is less than a predetermined threshold.

\* \* \* \* \*